US009358271B2

(12) United States Patent
Mitrovic et al.

(10) Patent No.: US 9,358,271 B2
(45) Date of Patent: *Jun. 7, 2016

(54) USE OF NATRIURETIC PEPTIDE FOR TREATING HEART FAILURE

(71) Applicant: Cardiorentis AG, Zug (CH)

(72) Inventors: Veselin Mitrovic, Bad Nauheim (DE); Hartmut Luss, Hannover (DE); Wolf-Georg Forssmann, Hannover (DE); Markus Meyer, Hannover (DE); Klaus Dohler, Hannover (DE)

(73) Assignee: Cardiorentis AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,350

(22) Filed: Feb. 26, 2015

(65) Prior Publication Data

US 2015/0224174 A1  Aug. 13, 2015

Related U.S. Application Data

(63) Continuation of application No. 14/218,389, filed on Mar. 18, 2014, now Pat. No. 9,023,794, which is a continuation of application No. 12/767,395, filed on Apr. 26, 2010, now Pat. No. 8,710,006, which is a continuation of application No. 11/400,696, filed on Apr. 7, 2006, now Pat. No. 7,732,406.

(60) Provisional application No. 60/669,786, filed on Apr. 7, 2005, provisional application No. 60/669,751, filed on Apr. 8, 2005, provisional application No. 60/732,585, filed on Nov. 1, 2005.

(51) Int. Cl.
*A61K 47/26* (2006.01)
*A61K 38/22* (2006.01)

(52) U.S. Cl.
CPC .............. *A61K 38/2242* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 4,751,284 A | 6/1988 | Forssmann | |
| 4,782,044 A | 11/1988 | Forssmann | |
| 4,895,932 A | 1/1990 | Forssmann | |
| 5,166,191 A | 11/1992 | Cronin et al. | |
| 5,449,751 A | 9/1995 | Forssmann et al. | |
| 5,461,142 A | 10/1995 | Forssmann et al. | |
| 5,514,670 A | 5/1996 | Friedman et al. | |
| 5,571,789 A | 11/1996 | Fluge et al. | |
| 5,741,776 A | 4/1998 | Clark et al. | |
| 5,767,239 A | 6/1998 | Immer et al. | |
| 6,407,211 B1 | 6/2002 | Burnett et al. | |
| 6,831,064 B1 | 12/2004 | Forssmann et al. | |
| 7,595,313 B2 | 9/2009 | Garvey et al. | |
| 7,662,773 B2 | 2/2010 | James et al. | |
| 7,732,406 B2 * | 6/2010 | Mitrovic et al. | 514/16.4 |
| 8,067,464 B2 | 11/2011 | Garvey | |
| 8,710,006 B2 * | 4/2014 | Mitrovic et al. | 514/12.4 |
| 9,023,794 B2 * | 5/2015 | Mitrovic et al. | 514/12.4 |
| 2004/0063630 A1 | 4/2004 | Schreiner | |
| 2004/0203081 A1 | 10/2004 | James et al. | |
| 2005/0113286 A1 | 5/2005 | Schreiner et al. | |
| 2006/0008415 A1 | 1/2006 | Kaisheva et al. | |
| 2008/0004206 A1 | 1/2008 | Rosen et al. | |
| 2008/0181903 A1 | 7/2008 | Bhaskar et al. | |
| 2010/0168011 A1 | 7/2010 | Jennings, Jr. et al. | |
| 2010/0204107 A1 | 8/2010 | Bevec | |
| 2011/0014180 A1 | 1/2011 | Koide et al. | |
| 2011/0065676 A1 | 3/2011 | Perelman et al. | |
| 2011/0077381 A1 | 3/2011 | Osterkamp et al. | |
| 2011/0112038 A1 | 5/2011 | Hellberg et al. | |
| 2011/0282030 A1 | 11/2011 | Dickey et al. | |
| 2012/0052097 A1 | 3/2012 | Fetzer et al. | |
| 2012/0093814 A1 | 4/2012 | Canada et al. | |
| 2012/0114659 A1 | 5/2012 | Waterman et al. | |
| 2013/0197188 A1 | 8/2013 | Forssmann et al. | |

FOREIGN PATENT DOCUMENTS

| | | |
|---|---|---|
| EP | 349545 | 1/1990 |
| WO | 9845329 | 10/1998 |
| WO | 02/28418 | 4/2002 |
| WO | 2006110743 | 10/2006 |
| WO | 2009034134 | 3/2009 |
| WO | 2009086126 | 7/2009 |
| WO | 2009086166 | 7/2009 |
| WO | 2011113825 | 9/2011 |

OTHER PUBLICATIONS

Elsner et al., American Heart Journal, 1995, 129(4), 766-773.*
Abassi et al., Renal and systemic effects of urodilatin in rats with high-output heart failure, Am. J. Physiol. Renal Physiol. 262: 615-21 (1992).
Akhter et al., Effect of elevated admission serum creatinine and its worsening on outcome in hospitalized patients with decompensated heart failure, Am. J. Cardiol. 94(7): 957-60 (2004).
Aliti et al., Aggressive Fluid and Sodium Restriction in Acute Decompensated Heart Failure, JAMA 2013; 173:1058-1064.
Arcand et al., A high-sodium diet is associated with acute decompensated heart failure in ambulatory heart failure patients: a prospective follow-up study, Am. J. Clin. Nutr. 2011:93:322-337.
Bestle et al., Cardiovascular, endocrine, and renal effects of urodilatin in normal humans, Am. J. Physiol. Regulatory Integrative Comp. Physiol. 276: 684-95 (1999).

(Continued)

*Primary Examiner* — James H Alstrum Acevedo
*Assistant Examiner* — Roy Teller
(74) *Attorney, Agent, or Firm* — Lowenstein Sandler LLP

(57) ABSTRACT

The present invention relates to the use of a natriurectic peptide, such as urodilatin, for treating a patient suffering from heart failure, such as acute decompensated heart failure. Preferably, a composition comprising an effective amount of urodilatin is intravenously administered to the patient continuously through a time period of at least 24 hours and up to 120 hours, preferably at least 48 hours.

19 Claims, 17 Drawing Sheets

(56) References Cited

OTHER PUBLICATIONS

Brookes, L., SIRIUS II: Safety and Efficacy of an Intravenous Placebo-Controlled Randomized Infusion of Ularitide in a Prospective Double-Blind Study in Patients with Sympotomatic, Decompensated Chronic Heart Failure (Phase IIb), Oct. 2005, Retrieved from the Internet—URL: http://www.medscape.com/viewarticle/514120.

Brunner-La Rocca et al., Therapeutic benefits of increasing natriuretic peptide levels, Cardiovasc Res vol. 51, pp. 510-520 (2001).

Burger et al., Effect of nesiritide (B-type natriuretic peptide) and dobutamine on ventricular arrhythmias in the treatment of patients with acutely decompensated congestive heart failure: The PRECEDENT study, Am. Heart J. 144: 1102-08(2002).

Cleland, John, G.F., et al. Clincial Trials Update from the European Society of Cardiology Meeting 2005: Care-HF Extension Study, ESSENTIAL, CIBIS-III, S-ICD, ISSUE-2, STRIDE-2, SOFA, IMAGINE, PREAMI, SIRIUS-II and ACTIVE; The European Journal of Hear Failure; 2005; vol. 7, pp. 1070-1075.

Cowie et al., Clinical applications of B-type natriuretic peptide (BNP) testing, Eur. Heart J. 24(19): 1710-18 (2003).

deGoma EM et al., Emerging Therapies Management of Decompensated: From Bench to Bedside, Journal of the American College of Cardiology, vol. 48, No. 12, pp. 2397-2409 (2006).

Dorner et al., Hemodynamic effects of continuous urodilatin infusion: A dose-finding study, Clin. Pharmacol. Ther. 54(3): 322-30 (1998).

Elkayam et al., Nesiritide: A New Drug for the Treatment of Decompensated Heart Failure, J. Cardiovasc. Pharmacol. Ther., vol. 7, No. 3, pp. 181-194 (Sep. 2002).

European Search Report for European Patent Application No. 12156696.2, issued Sep. 19, 2012.

Forssmann et al., The renal urodilatin system: clinical implications, Cardiovasc. Res. 51(3): 450-62 (2001).

Francis, Acute decompensated heart failure: The cardiorenal syndrome, Clev. Clin. J. Med. 73(Supp. 2): S8-S13 (2006).

Gagelmann et al., Urodilatin (CDD/ANP-95-126) is not biologically inactivated by a peptidase from dog kidney cortex membranes in contrast to atrial natriuretic peptide/cardiodilatin ($\alpha$-hANP/CDD-99-126), FEBS Lett. 233(2): 249-54 (1988).

Gheorghiade M, Pang PS, "Acute Heart Failure Syndromes," Journal of the American College of Cardiology, vol. 53, pp. 557-573 (2009).

Greenberg et al., Nucleotide sequence of the gene encoding human atrial natriuretic factor precursor, Nature 312 (5995): 656-58 (1984).

Ha et al., Dendroaspis natriuretic peptide protects the post-ischemic myocardial injury, Regul. Pept. 133: 13-19 (2006).

Hobbs et al., Hemodynamic Effects of a Single Intravenous Injection of Synthetic Human Brain Natriuretic Peptide in Patients With Heart Failure Secondary to Ischemic or Idiopathic Dilated Cardiomyopathy, Am. J. Cardiol. 78(8): 396-901 (1996).

Hummel, M., et al., "Urodilatin: A New Peptide with Beneficial Effects in the Postoperative Therapy of Cardiac Transplant Recipients", Clinical Investigator, vol. 70, No. 8, Aug. 1992, p. 674-682.

Kajimoto K et al., "Efficacy of carperitide, a recombinant human atrial natriuretic peptide, alone therapy in patients with acutely decompensated congestive heart failure," Eur. Heart Journal, vol. 25 (Suppl.):73/Abstract P505 (Sep. 2004).

Kentsch et al., Haemodynamic and renal effects of urodilatin bolus injections in patients with congestive heart failure, Eur. J. Clin. Invest. 22(10): 662-69 (1992).

Kentsch et al., Severe hypotension and bradycardia after continuous intravenous infusion of urodilatin (ANP 95-126) in a patient with congestive heart failure, Eur. J. Clin. Invest. 25(4): 281-83 (1995).

Levin et al., Natriuretic Peptides, New England Journal of Medicine, vol. 339, No. 5, pp. 321-328 (1998).

Luss et al., Ularitide Improves Hemodynamics and Dyspnea in Patients with Decompensated Congestive Heart Failure without Deleterious Effect on Renal Function (Meeting Abstract), Circulation 112(17 Supp. II): 425 (2005).

Luss et al., "Renal Effects of Ularitide in Patients with Decompensated Heart Failure," American Heart Journal, vol. 155, No. 6, pp. 1012.e1-9 (Jun. 2008).

Michels, P. et al., "J. Natriuretische Peptide: Physiologische, pathophysiologische und klinische Aspekte= Natriuretic peptides: Physiological, pathophysiological and Clinical Aspects," Natriuretische Peptide: Physiologische, pathophysiologische und klinische Aspekte= Natriuretic peptides: Physiological, pathophysiological and Clinical Aspects. AINS. Anästhesiologie, Intensivmedizin, Notfallmedizin, Schmerztherapie, vol. 36, No. 7, pp. 406-416 (2001) (with English translation).

Mills et al., Sustained hemodynamic effects of an infusion of nesiritide (human b-type natriuretic peptide) in heart failure: A randomized, double-blind, placebo-controlled clinical trial, J. Am. Coll. Cardiol. 34(1): 155-62 (1999).

Mitrovic et al., "Effects of the renal natriuretic peptide urodilatin (ularitide) in patients with decompensated chronic heart failure: A double-blind, placebo-controlled, ascending-dose trial," American Heart Journal, vol. 150, No. 6, pp. 1239.e1-1239.e8 (Dec. 2005).

Mitrovic, V., et al., Haemodynamic and Clinical Effects of Ularitide in Decompensated Heart Failure, European Heart Journal, vol. 27, (2006), p. 2823-2832.

Mitrovic et al., Hemodynamic and neurohumoral effects of urodilatin in patients with decompensated congestive heart failure. Abstract from German Journal of Cardiology of 70th Annual Meeting of the German Society of Cardiology—Cardiac and Cardiovascular Research of Apr. 15-17, 2004, Mannheim. Z Kardiol 93 (suppl 3): III-423 V1580Z, 2004; Abstract V1580.

Mitrovic et al., Haemodynamic and neurohumoral effects of the renal natriuretic peptide urodilatin in patients with decompensated congestive heart failure. Abstract from Heart Failure Updated 2004, "From Hippocrates to Hypotheses," Wroclaw, Poland Jun. 12-15, 2004. Eur. Journal of Heart Failure Supplements, vol. 3(1): 80-81; Abstract 323, 2004.

Mitrovic, V., et al., "Role of Guanylate Cyclase Modulators in Decompensated Heart Failure", Heart Failure Review, vol. 14, (2009), p. 309-319.

Mitrovic et al., Ularitide Exerts Beneficial Hemodynamic Effects and Improves Symptoms in Patients with Decompensated Congestive Heart Failure (Meeting Abstract), Circulation 112(17 Supp. II): 453-54 (2005).

Mitrovic, V., et al., "Urodilatin Induces cGMP-Mediated Haemodynamic Effects in Patients with Decompensated Congestive Heart Failure", European Heart Journal, vol. 25, Aug. 2004, p. 452.

Motrovic et al., Urodilatin induces cGMP-mediated haemodynamic effects in patients with decompensated congestive heart failure. Abstract from ESC Congress 2004. Eur. Heart Journal, 25 (Suppl):425; Abstract 2639, Aug. 2004.

Mitrovic et al., Urodilatin induces cGMP-mediated haemodynamic effects in patients with decompensated congestive heart failure (Press Release), Deutsche Gesellschaft fur Kardiologie—Herz—und Kreislaufforschunt e.V. (DGK), 2004.

Mohacsi, P et al., "Die therapierefraktäre Herzinsuffizienz: etablierte und neue Behandlungsmöglichkeiten," Die therapierefraktäre Herzinsuffizienz: etablierte und neue Behandlungsmöglichkeiten. Schweiz Med Forum, vol. 3, pp. 1224-1236 (2003) (with English translation).

Müller, C. et al., "B-Typ-natriuretisches Peptid," B-Typ-natriuretisches Peptid. Herz, vol. 28, No. 5, pp. 374-379 (2003) (with English translation).

Munzel et al., Mechanisms involved in the response to prolonged infusion of atrial natriuretic factor in patients with chronic heart failure, Circulation 83(1): 191-201 (1991).

Nakayama et al., mRNA sequence for human cardiodilatin-atrial natriuretic factor precursor and regulation of precursor mRNA in rat atria, Nature 310(5979): 699-701 (1984).

Northridge et al., Atrial natriuretic factor in chronic heart failure, Herz 16(2): 92-101 (1991).

Oikawa et al., Cloning and sequence analysis of cDNA encoding a precursor for human atrial natriuretic poly peptide, Nature 309(5970): 724-26 (1984).

(56) References Cited

OTHER PUBLICATIONS

Parikh, C., et al., "Prevention of Acute Renal Failure (ARF) Following Allogeneic Myeloablative Hematopietic Urodilatin and Mannitol: A Phase II Trial", Journal of the American Society of Nephrology, vol. 14, (2003), p. 355A.
Publication Committee for the VMAC Investigators, Intravenous Nesiritide vs Nitroglycerin for Treatment of Decompensated Congestive Heart Failure: A Randomized Controlled Trial, JAMA 287(12): 1531-40 (2002).
Riegger et al., Effects of ANP-(95-126) in dogs before and after induction of heart failure, Am. J. Physiol. Heart Circ. Physiol. 259: H1643-48 (1990).
Sackner-Bernstein et al., Risk of Worsening Renal Function With Nesiritide in Patients With Acutely Decompensated Heart Failure, Circulation 111(112): 1487-91 (2005).
Saxenhofer et al., Urodilatin, a natriuretic factor from kidneys, can modify renal and cardiovascular function in men, Am. J. Physiol. Renal Physiol. 259: 832-38 (1990).
Schäfer, S. et al., "A. Neue Wirkstoffe und Therapiekonzepte: Behandlung von Bluthochdruck und Herzinsuffizienz," Neue Wirkstoffe und Therapiekonzepte: Behandlung von Bluthochdruck und Herzinsuffizienz. Pharmazie in unserer Zeit, vol. 32, No. 1, pp. 54-59 (2003) (with English translation).
Schulz-Knappe et al., Isolation and structural analysis of "urodilatin", a new peptide of the cardiodilatin-(ANP)-family, extracted from human urine, Klin. Wochenschr. 66(17): 752-59 (1988).
Seidman et al., Molecular studies of the atrial natriuretic factor gene, Hypertension 7(3 pt. 2): 131-34 (1985).
Stanek, B., "ESC-Kongreβ 2003, Wien, Satellitensymposium: Recombinant Human BNP," ESC-Kongreβ 2003, Wien, Satellitensymposium: Recombinant Human BNP. Journal of Cardiology, vol. 10, No. 10, pp. 456-457 (2003) (with English translation).
Takahashi et al., Cyclic GMP Production by ANP, BNP, and NO during Worsening and Improvement of Chronic Heart Failure, Jpn. Heart J. 44(5): 713-24 (2003).
Vesely, Natriuretic peptides and acute renal failure, Am. J. Physiol. Renal Physiol. 285: F167-F177 (2003).
Wang et al., Nesiritide Does Not Improve Renal Function in Patients With Chronic Heart Failure and Worsening Serum Creatinine, Circulation 110: 1620-25 (2004).
Elsner et al., Efficacy of prolonged infusionof urodilatin [AND-(95-126)] in patients with congestive heart failure, American Heart Journal, 1995, vol. 129, No. 4, pp. 766-773.
International Search Report for PCT/IB2014/000253 mailed Nov. 14, 2014, 21 pgs.
Koichi Shimamura et al., Acute efficacy of low-dose human atrial natriuretic peptide monotherapy without loop diuretics for acute decompensated hear failure with left ventricular systolic dysfunction: A case report, International Journal of Cardiology, vol. 143, No. 2, Aug. 1, 2010, pp. e21-e23.
Armstrong et al., A Canadian context fo the Acute Study of Clinical Effectiveness of Nesiritide and Decompensated Heart Failure (ASCENDHF) trial, Can J. Cardiol. 24, Suppl. B, 30B-32B, 2008.
Bani et al. Basic Progress and Future Therapeutic Perspectives of Relaxin in Ischemic Heart Disease, Ann. N.Y. Acad. Sci. 1041, 423-430, 2005.
Clinical trial: Efficacy and Safety of Ularitide for the Treatment of Acute Decompensated Heart Failure (TRUE-AHF), NCT01661634, Jul. 31, 2012.
Committee for VMAC Investigators, Intravenous Nesiritide vs Nitroglycerin for treatment of decompensated congestive heart failure, JAMA, 287, 1531-1540, 2002.
Dschietzig et al. Relaxin-a pleiotropic hormone and its emerging role for experimental and clinical therapeutics, Pharmacology & Therapeutics 112, 38-56, 2006.
Dschietzig et al. Relaxin improves TNF-a-induced endothelial dysfunction: the role of glucocorticoid receptor and phosphatidylinositol 3-kinase signaling, Cardiovascular research, 95, 97-107, 2012.
Forssmann W-G et al. The endocrine heart and the natriuretic peptides: histochemistry, cell biology, and functional aspects of the renal urodilatin system, Histochem. Cell Biol. 110, 335-357, 1998.
Li et al., Tumor necrosis factor-a in mechanic trauma plasma mediates cardiomyocyte apoptosis. Am J Physiol Heart Circ Physiol 293: H1847-H1852, 2007.
Moore et al. Relaxin Antagonizes Hypertrophy and Apoptosis in Neonatal Rat Cardiomyocytes, Endocrinology, 148, 1582-1589, 2007.
Samuel et al., Drugs of the future: the hormone relaxis. Cell Mol. Life Sci. 64, 1539-1557, 2007.
Silver et al. BNP Consensus Panel 2004: A Clinical Approach for the Diagnostic, Prognostic, Screening, Treatment Monitoring, and Therapeutic Roles of Natriuretic Peptides in Cardiovascular Diseases. Congestive Heart Failure, 10, Suppl. 3, 1-30, 2004.
Song et al., Tumor necrosis factor-alpha induces apoptosis via inducible nitric oxide synthase in neonatal mouse cardiomyocytes. Cardiovasc. Res. 45, 595-602, 2000.
Written Opinion for PCT/IB2014/000253, dated Jan. 24, 2014.
Grossman, et al., "Relaxin: a new approach for the treatment of acute congestive heart failure." Cardiol. Rev., 2010, 18: 305-3012.
Australian Examination Report for Patent Application No. 2014208851, mailed Jan. 11, 2016, 5 pgs.

\* cited by examiner

FIG. 2

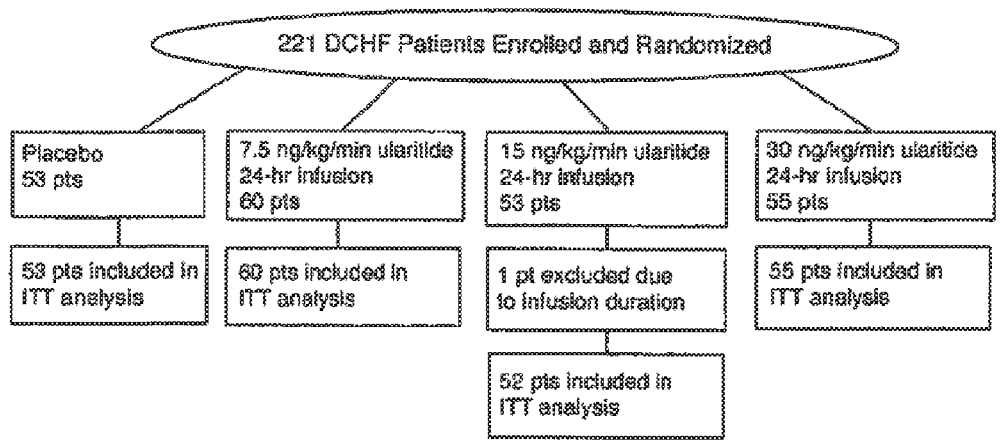

Demographic and Baseline Characteristics

| Demographics | All subjects (n=220) |
|---|---|
| Age - mean, years | 61 |
| Male/Female (%) | 78/22 |
| EF < 30% (%) | 72 |
| EF < 40% (%) | 94 |
| Baseline Hemodynamics | |
| PCWP - mean, mmHg | 25 |
| PAP - mean, mmHg | 37 |
| RAP - mean, mmHg | 11 |
| SVR - mean, dyn/sec/cm$^5$ | 1863 |
| CI mean, l/min/m$^2$ | 1.9 |
| Systolic BP - mean, mmHg | 125 |

Renal Function at Baseline

| Mean ± SD | Placebo (n=53) | 7.5 ng/kg/min (n=60) | 15 ng/kg/min (n=52) | 30 ng/kg/min (n=55) |
|---|---|---|---|---|
| Serum creatinine [mg/dL] (n) | 1.25 ± 0.42 (52) | 1.19 ± 0.37 (59) | 1.23 ± 0.35 (51) | 1.22 ± 0.37 (53) |
| BUN [mg/dL] (n) | 37.1 ± 29.1 (51) | 40.8 ± 32.1 (58) | 35.6 ± 21.9 (50) | 45.6 ± 34.1 (54) |
| Creatinine clearance [mL/min] (n) | 78.3 ± 34.1 (52) | 85.4 ± 36.6 (59) | 78.2 ± 35.9 (51) | 75.3 ± 30.3 (53) |
| GFR [mL/min] (n) | 55.6 ± 23.6 (37) | 60.3 ± 21.1 (41) | 52.8 ± 18.3 (36) | 53.6 ± 16.2 (37) |

USE OF NATRIURETIC PEPTIDE FOR TREATING HEART FAILURE

RELATED APPLICATIONS

This application is a continuation of U.S. patent application Ser. No. 14/218,389, filed Mar. 18, 2014, which is a continuation of U.S. patent application Ser. No. 12/767,395, filed Apr. 6, 2010, now U.S. Pat. No. 8,710,006, which is a continuation of U.S. application Ser. No. 11/400,696 filed Apr. 7, 2006, now U.S. Pat. No. 7,732,406, which claims priority to U.S. Provisional Application No. 60/669,786, filed Apr. 7, 2005, 60/669,751, filed Apr. 8, 2005, and 60/732,585, filed Nov. 1, 2005, each of which is incorporated herein by reference in its entirety.

BACKGROUND OF THE INVENTION

A family of related peptides has been discovered that works in concert to achieve salt and water homeostasis in the body. These peptides, termed natriuretic peptides for their role in moderating natriuresis and diuresis, have varying amino acid sequences and originate from different tissues within the body. This family of natriuretic peptides consists of atrial natriuretic peptide (ANP), brain natriuretic peptide (BNP), Ctype natriuretic peptide (CNP), Dendroaspis natriuretic peptide (DNP), and urodilatin (URO, or ularitide). Their tissue-specific distribution is as follows: heart (ANP, BNP, and DNP); brain (ANP, BNP, and CNP); endothelial cells (CNP); plasma (DNP); and kidney (URO). These peptides are constituents of a hormonal system that plays a critical role in maintaining an intricate balance of blood volume/pressure in the human body. For instance, urodilatin, a close analog of ANP secreted by kidney tubular cells, promotes excretion of sodium and water by acting directly on kidney cells in the collecting duct to inhibit sodium and water reabsorption. Like other natriuretic peptides, such as ANP and BNP, urodilatin has been studied for use in treating various conditions, including renal failure or congestive heart failure (see, e.g., U.S. Pat. Nos. 25 5,571,789 and 6,831,064; Kentsch et al., *Eur. J. Clin. Invest.* 1992, 22(10):662-669; Kentsch et al., *Eur. J. Clin Invest.* 1995, 25(4):281-283; Elsner et al., *Am. Heart J.* 1995, 129(4):766-773; and Forssmann et al., *Clinical Pharmacology and Therapeutics* 1998, 64(3):322-330).

Cardiovascular diseases are the leading causes of death in the United States, regardless of gender or ethnicity. Among these diseases, congestive heart failure (CHF) is highly prevalent. According to the American Heart Association, the number of hospital discharges and the number of deaths due to CHF both rose roughly 2.5-fold from 1979 to 1999. Currently, about 5 million Americans have been diagnosed with CHF, and about 550,000 new cases occur annually (American Heart Associate 2001). This life-threatening condition is accompanied by great financial impact. Thus, there exists a need for providing new and more effective methods for treating heart failure.

Previous studies have shown that the administration of ularitide is effective in treating heart failure patients. The present inventors have discovered a new method for ularitide administration that is surprisingly effective for treating heart failure of varying causes, particularly acute decompensated heart failure. The method of this invention can also be used for treating heart conditions that generally relate to abnormal fluid accumulation in the heart, e.g., myocardial edema.

BRIEF SUMMARY OF THE INVENTION

The present invention relates to a method for treating heart failure. The method comprises the step of administering an effective amount of a natriuretic peptide, e.g., urodilatin, where such administration is continuous over a time period of at least 24 hours, preferably from 24 hours to 120 hours, and more preferably, from 24 hours to 48 hours, or at least 48 hours, such as from 48 hours to 60 hours, or, most preferably, from 48 hours to 72 hours. A preferred means for administering the natriuretic peptide is by intravenous administration. Other means of delivering the natriuretic peptide, such as by oral ingestion, are also available for the practice of this invention. For intravenous administration, the method preferably does not include a bolus infusion of a natriuretic peptide, such that no potential impairment of kidney function will result. Kidney function can be impaired by heart failure and can result from impaired blood perfusion through the kidneys due to insufficient pumping action of the heart. For example, recombinant BNP (Natrecor) is given to heart failure patients via a high dose intravenous bolus application followed by a lower dose intravenous infusion. Recent studies have shown that Natrecor application in heart failure may increase the risk of worsening renal function (Sackner-Bernstein et al., *Circulation* 2005, 111:1487-1491). Impaired kidney function can be assessed and monitored by measuring serum creatinine or blood urea nitrogen (BUN), which are increased when kidney function is impaired or the kidneys are injured. Furthermore, glomerular filtration rate or calculated creatinine clearance rate are reduced when renal function is impaired. Increased serum creatinine of just 0.1 mg/dl independently of baseline levels or transient increases in creatinine levels of 0.3 to 0.5 mg/dl are predictive for worsened outcome in acutely decompensated heart failure. Natrecor caused increases of serum creatinine in patients with heart failure (Sackner-Bernstein et al., supra). The exact mechanism by which Natrecor may negatively affect kidney function is presently unknown. It is likely that upon bolus application of Natrecor, blood perfusion through the kidneys decreases, thus leading to impaired kidney function and kidney injury.

In one embodiment, the invention provides a method for treating heart failure, such as acute decompensated heart failure, or chronic congestive heart failure. This method includes the step of administering to a patient a composition comprising an effective amount of a natriuretic peptide (e.g., urodilatin) continuously for a time period of at least 24 hours, more preferably 24 to 120 hours or 48 to 120 hours. In some cases, the administration is by intravenous infusion. In some other cases, the time period for administration may be from 24 hours to 48 hours, or 48-60 hours, or 48-72 hours, or 48-96 hours, or 72-96 hours, or 72-120 hours. For example, administration of the natriuretic peptide may last 24 hours, 36 hours, 48 hours, 60 hours, 72 hours, 96 hours, 120 hours, or any desirable time duration within this range.

In one embodiment of the invention, the natriuretic peptide used in the method is ularitide or urodilatin. Alternatively, the natriuretic peptide may be atrial natriuretic peptide (ANP), brain natriuretic peptide (BNP), C-type natriuretic peptide (CNP), or Dendroaspis natriuretic peptide (DNP).

The administration rate may be 7.5 ng/(kg·min), 15 ng/(kg·min), 30 ng/(kg·min), 45 ng/(kg·min), 60 ng/(kg·min), 100 ng/(kg·min), 200 ng/(kg·min), or up to 1 mg/(kg·min). Preferably, urodilatin is administered at a rate of 15 ng/(kg·min).

In another embodiment, one or more different cardiac medicines is administered to the patient. These one or more different cardiac medicines may be administered in combination with the natriuretic peptide (e.g., urodilatin), for example, by the same route (e.g., intravenously), with the option of being in one single pharmaceutical composition or two or more separate compositions; or these one or more different cardiac medicines may be administered separately by a different means (e.g., by oral ingestion).

The composition used in the method of this invention optionally further comprises a pharmaceutically acceptable excipient or carrier. For example, mannitol may be used in such a pharmaceutical composition. In an exemplary embodiment, the concentration of mannitol is 10 times of the concentration of natriuretic peptide, such as urodilatin. In another exemplary embodiment, the composition is an aqueous solution of 0.9% NaCl in which natriuretic peptide, such as urodilatin, and mannitol are dissolved. In one particular embodiment of the method, the composition is an aqueous solution of 0.9% NaCl in which urodilatin and mannitol are dissolved, the rate of urodilatin infusion is 15 ng/(kg·min), and the time period for continuous infusion is 24 hours.

In another aspect, the present invention provides the use of a natriuretic peptide, such as urodilatin, for the manufacture of a medicament for the treatment of heart failure, which includes acute decompensated heart failure and chronic congestive heart failure. The medicament may contain, in addition to an effective amount of the active ingredient (i.e., a natriuretic peptide, such as urodilatin), a pharmaceutically acceptable excipient or carrier. Preferably, the medicament is formulated for continuous intravenous administration over a time period of at least 24 hours, more preferably from 24 hours to 120 hours. In some cases, the medicament is formulated for a sustained release of the natriuretic peptide over a period of at least 24 hours. In some embodiments, the time period for administration may be 24 to 72 hours, 48 to 72 hours. For example, the administration of the natriuretic peptide containing medicament may last 24 hours, 36 hours, 48 hours, 60 hours, 72 hours, 96 hours, 120 hours, or any desirable time duration within this range.

In some cases, the natriuretic peptide used in the medicament is urodilatin; in other cases, the natriuretic peptide may be atrial natriuretic peptide (ANP), brain natriuretic peptide (BNP), C-type natriuretic peptide (CNP), or Dendroaspis natriuretic peptide (DNP).

Preferably, the medicament is administered in a manner such that the patient is receiving the active ingredient (e.g., urodilatin) at a rate of at least 7.5 ng/(kg·min). In other embodiments, the administration rate is 7.5 ng/(kg·min), 15 ng/(kg·min), 30 ng/(kg·min), or 1 mg/(kg·min). In one preferred example, ularitide is administered at the rate of 15 ng/(kg·min).

In some cases, one or more different cardiac medicines is also administered to the patient. These one or more different cardiac medicines may be given to the patient in the same composition as the natriuretic peptide, e.g., urodilatin, or may be given to the patient in a separate composition.

The medicament often further comprises a pharmaceutically acceptable excipient or carrier, such as mannitol. In an exemplary embodiment, the concentration of mannitol in the medicament is 10 times of the concentration of natriuretic peptide, such as urodilatin. In another exemplary embodiment, the medicament is an aqueous solution of 0.9% NaCl in which natriuretic peptide, such as urodilatin and mannitol are dissolved. In one particular embodiment of the claimed method, the medicament administered to the patient is an aqueous solution of 0.9% NaCl in which urodilatin and mannitol are dissolved, and the medicament is infused into the patient at a rate of 15 ng/(kg·min) urodilatin continuously over the time period of 24 hours.

BRIEF DESCRIPTION OF THE DRAWINGS

FIG. 2: Study flow diagram and patient disposition; demographic data and baseline characteristics; renal function at baseline.

DEFINITIONS

Figure 1A:
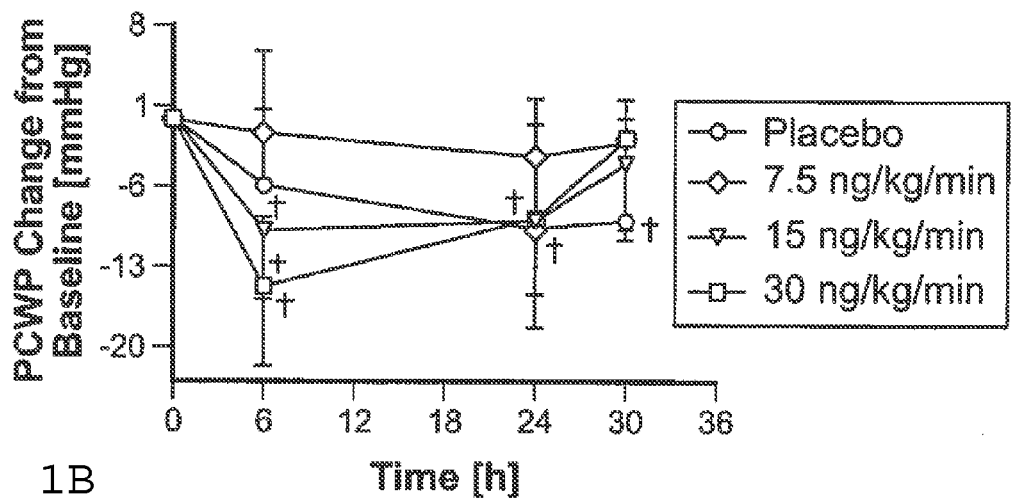
FIG. 1A: Graphical depiction of changes from baseline of PCWP, during placebo or ularitide infusion, and after discontinuation of infusion. Values are mean±SD, n=6, except for the placebo group at 30 hours (n=5) *P<0.05 versus placebo, † P<0.05 versus baseline.

As used herein, the term "heart failure" encompasses all types of cardiovascular conditions that, regardless of their cause, are generally recognized by a physician as heart failure, which include but are not limited to, acute heart failure, chronic heart failure, congestive heart failure, and particularly acute decompensated heart failure. In this application, the terms acute decompensated heart failure (ADHF) and decompensated heart failure (DHF) are used interchangeably.

These conditions typically involve weakened heart function combined with a build-up of body fluid and may be the result of either a sudden event, such as myocardial infarction or the rupture of a heart valve, or a chronic and slowly progressing process, such as the gradual weakening of heart muscles due to cardiomyopathy from infections or alcohol/drug abuse, and other pre-existing medical conditions such as hypertension, coronary artery disease, valve disease, thyroid disease, kidney disease, diabetes, or congenital heart defects. Also encompassed by the term "heart failure" are any heart conditions relating to fluid build-up in the heart, such as myocardial edema.

The term "administrate" or "administration," as used herein, encompasses various methods of delivering a composition containing a natriuretic peptide to a patient. Modes of administration may include, but are not limited to, methods that involve delivering the composition intravenously, intraperitoneally, intranasally, transdermally, topically, subcutaneously, parentally, intramuscularly, orally, or systemically, and via injection, ingestion, inhalation, implantation, or adsorption by any other means. The preferred means of administering a composition comprising a natriuretic peptide (e.g., ularitide) is intravenous injection, where the composition is formulated as a sterile solution. Another route of administration is oral ingestion, where the natriuretic peptide can be formulated as a pharmaceutical composition in the form of a syrup, an elixir, a suspension, a powder, a granule, a tablet, a capsule, a lozenge, a troche, an aqueous solution, a cream, an ointment, a lotion, a gel, or an emulsion. Preferably, the pharmaceutical composition for oral ingestion is formulated for sustained release over a period of at least 24 hours. Furthermore, administration of a natriuretic peptide can be achieved by subcutaneous injection of a natriuretic peptide-containing composition, which is prepared as a sustained release system comprising microspheres or biodegradable polymers, such that the natriuretic peptide can be released into a patient's body at a controlled rate over a period of time, e.g., at least 24 hours or 48 hours.

An "effective amount" refers to the amount of an active ingredient, e.g., urodilatin, in a pharmaceutical composition that is sufficient to produce a beneficial or desired effect at a level that is readily detectable by a method commonly used for detection of such an effect. Preferably, such an effect results in a change of at least 10% from the value of a basal level where the active ingredient is not administered, more preferably the change is at least 20%, 50%, 80%, or an even higher percentage from the basal level. As will be described below, the effective amount of an active ingredient may vary from subject to subject, depending on age, general condition of the subject, the severity of the condition being treated, and the particular biologically active agent administered, and the like. An appropriate "effective" amount in any individual case may be determined by one of ordinary skill in the art by reference to the pertinent texts and literature and/or by using routine experimentation.

The term "natriuretic peptide" refers to a peptide that has the biological activity of promoting natriuresis, diuresis, and vasodilation. Assays for testing such activity are known in the art, e.g., as described in U.S. Pat. Nos. 4,751,284 and 5,449,751. Examples of 25 natriuretic peptides include, but are not limited to, atrial natriuretic peptide (ANP(99-126)), brain natriuretic peptide (BNP), C-type natriuretic peptide (CNP), Dendroaspis natriuretic peptide (DNP), urodilatin (URO, or ularitide), and any fragments of the prohormone ANP(1-126) or BNP precursor polypeptide that retains the vasodilating, natriuretic, or diuretic activity. For further description of exemplary natriuretic peptides and their use or preparation, see, e.g., U.S. Pat. Nos. 4,751,284, 4,782,044, 4,895,932, 5,449,751, 5,461,142, 5,571,789, and 5,767,239. See also, Ha et al., *Regul. Pept.* 133(1-3):13-19, 2006.

As used in this application, the term "urodilatin" refers to a 32~amino acid peptide hormone that is described by U.S. Pat. No. 5,449,751 and has the amino acid sequence set forth in GenBank Accession No. 1506430A. Urodilatin, the 95~126 fragment of atrial natriuretic peptide (ANP), is also referred to as ANP(95-126). The term "atrial natriuretic peptide" or "ANP(99-126)" refers to a 28-amino acid peptide hormone, which is transcribed from the same gene and derived from the same polypeptide precursor, ANP(1-126), as urodilatin but without the first four amino acids at the N-terminus. For a detailed description of the prohormone, see, e.g., Oikawa et al. (*Nature* 1984; 309:724-726), Nakayama et al. (*Nature* 1984; 310:699-701), Greenberg et al. (*Nature* 1984; 312:656-658), Seidman et al. (*Hypertension* 1985; 7:31-34) and GenBank Accession Nos. 1007205A, 1009248A, 1101403A, and AAA35529. Conventionally, the term urodilatin (URO) is more often used to refer to the naturally occurring peptide, whereas the term ularitide is often used to refer to the recombinantly produced or chemically synthesized peptide. In this application, the term "urodilatin" and "ularitide" are used interchangeably to broadly encompass both a naturally occurring peptide and a recombinant or synthetic peptide. The terms also encompass any peptide of the above-cited amino acid sequence containing chemical modification (e.g., deamination, phosphorylation, PEGylation, etc.) at one or more residues or substitution by the corresponding D-isomer(s), so long as the peptide retains the biological activity as a natriuretic peptide. Furthermore, a chemically modified urodilatin or ularitide may contain one or two amino acid substitutions for the purpose of facilitating the desired chemical modification (e.g., to provide a reactive group for conjugation). "Urodilatin" or "ularitide" of this application, regardless of whether it contains chemical modifications, retains a substantial portion, i.e., at least 50%, preferably at least 80%, and more preferably at least 90%, of the biological activity of the naturally-occurring wild-type urodilatin or ANP(95-126).

The term "cardiac medicine" refers to a therapeutic agent that is useful for treating a cardiac condition. A "cardiac medicine" includes but is not limited to natriuretic peptides, ACE inhibitors (ACEIs), beta-adrenergic blocking agents (beta-blockers), vasodilators, diuretics, digitalis preparations (e.g., digoxin), dopamine, dobutamine, levosimendan, nesiritide, blood thinners, angiotensin II receptor blockers, calcium channel blockers, nitrates, and potassium.

The term "pharmaceutically acceptable excipient or carrier" refers to any inert ingredient in a composition that may act, for example, to stabilize the active ingredient. A pharmaceutically acceptable excipient can include, but is not limited to, carbohydrates (such as glucose, sucrose, or dextrans), antioxidants (such as ascorbic acid or glutathione), chelating agents, low molecular weight proteins, high molecular weight polymers, gel-forming agents, or other stabilizers and additives. Other examples of a pharmaceutically acceptable carrier include wetting agents, emulsifying agents, dispersing agents, or preservatives, which are particularly useful for preventing the growth or action of microorganisms. Various preservatives are well known and include, for example, phenol and ascorbic acid. Examples of carriers, stabilizers, or adjuvants can be found in Remington's Pharmaceutical Sciences, Mack Publishing Company, Philadelphia, Pa., 17th ed. (1985).

As used herein, a "patient" refers to a human or a non-human mammal.

In this application, the word "between" is used in an inclusive manner with regard to the start and end points. In other words, when a time period is described as "between 24 to 48 hours," both times points of 24 hours and 48 hours are included in the time period.

DETAILED DESCRIPTION OF THE INVENTION

Natriuretic peptides such as ANP(99~126), urodilatin, and brain natriuretic peptide (BNP) have been used for treating various medical conditions. While the art teaches the administration of ularitide either as one or more high dose intravenous bolus (Kentsch et al., *Eur. J. Clin. Invest.* 1992, 22(10): 662-669) or continuous infusion over a period of 5 or 10 hours (Domer et al., *Clin Pharmacal Ther.,* 1998, 64(3):322-330; Elsner et al., *Am. Heart J.* 20 1995, 129(4):766-773), the present inventors discovered that, surprisingly, a continuous administration of ularitide at a low concentration over a prolonged time period (e.g., from 24 hours to 120 hours) provides superior efficacy, particularly because such low dose, continuous administration allows the treatment method to achieve the desired results while avoiding adverse side effects such as potential damage to kidney due to lower blood pressure.

The administration of a natriuretic peptide according to the present invention is preferably achieved by intravenous injection, subcutaneous injection, or oral ingestion. For intravenous administration, the composition comprising a natriuretic peptide may be formulated with an aqueous diluent, suitably mixed with other optional additives such as a surfactant and/or a preservative for proper fluidity, stability, and sterility of the composition, necessary for easy storage and injection. The injectable solution containing a natriuretic peptide may be prepared using a solvent or dispersion medium including water, ethanol, polyol (e.g., glycerol, propylene glycol, and liquid polyethylene glycol, and the like), suitable mixtures thereof, and/or vegetable oils. Proper fluidity may be maintained, for example, by the use of a coating material, such as lecithin, by the maintenance of the required particle size in the case of dispersion and by the use of surfactants. The prevention of the proliferation of microorganisms can be facilitated by various antibacterial and antifungal agents, for example, parabens, chlorobutanol, phenol, sorbic acid, thimerosal, and the like. In many cases, it is preferable to include isotonic agents, for example, sugars or sodium chloride. Prolonged absorption of the injectable compositions can be brought about by the use in the compositions of agents delaying absorption, for example, aluminum monostearate and gelatin. The injectable solution should be suitably buffered if necessary and the liquid diluent first rendered isotonic with sufficient saline or glucose. Lastly, the injectable solution, once prepared by incorporating the active ingredients in the required amount in the appropriate solvent with optional excipients, is sterilized using a method that does not inactivate the active ingredient(s) of the composition, e.g., by filtered sterilization.

For oral administration, the composition comprising a natriuretic peptide may be formulated with an inert diluent or with an assimilable edible carrier, or it may be enclosed in hard- or soft-shell gelatin capsule, or it may be compressed into tablets. The active ingredients (e.g., ularitide) may be incorporated with excipients and used in the form of ingestible tablets, buccal tables, troches, capsules, caplets, elixirs, suspensions, syrups, wafers, and the like. The orally ingestible formulation preferably contains high molecular weight polymers or gel-forming agents that allows sustained release of the natriuretic peptide over an extended period of time, for example, at least 24 hours. This sustained release system achieves the slow release of the active ingredient over a period of time, either as a controlled release system, which is effective in maintaining substantially constant level of the natriuretic peptide (e.g., urodilatin) in the blood, or as a prolonged release system, which, although unsuccessful at achieving substantially constant blood level of a natriuretic peptide, but nevertheless extends the duration of action of the natriuretic peptide over that time period.

The following examples are provided by way of illustration only and not by way of limitation. Those of skill in the art will readily recognize a variety of non-critical parameters that could be changed or modified to yield essentially the same or similar results.

EXAMPLES

Example 1

The aim of this study was to define the role of 24-hour infusions of ularitide in the treatment of acute decompensated heart failure (ADHF). In this randomized, double-blind, ascending-dose safety study, 24 patients with ADHF (cardiac index $1.91 \pm 0.34$ Umin per square meter, pulmonary capillary wedge pressure $26 \pm 6$ mm Hg, right atrial pressure $11 \pm 4$ mm Hg) received ularitide (7.5, 15, or 30 ng/(kg·min)) or placebo infusion over 24 hours.

Introduction

Urodilatin (ularitide) is a natriuretic peptide composed of 32 amino acid residues which was isolated from human urine (Schulz-Knappe P et al., *Klin Wochenschr,* 66:752-9 (1988)). After synthesis in the distal tubular cells, urodilatin is luminally secreted, binds further downstream in the inner medullary collecting duct to natriuretic peptide type A receptors, increases intracellular cyclic guanosine monophosphate (cGMP) levels, and thereby regulates renal sodium and water excretion (Forssmann W et al., *Cardiovasc Res,* 51:450-62 (2001)).

Urodilatin administered intravenously (N) to rats (Abassi Z A, et al., *Am J Physiol,* 262:F615-21 (1992)), dogs, (Riegger G A et al., *Am J Physiol,* 259:H1643-8 (1990)) or healthy volunteers (Saxenhofer H et al., *Am J Physiol,* 259:F832-8 (1990)) exhibits hemodynamic as well as diuretic and natriuretic effects. As is also known for other natriuretic peptides, urodilatin effects are mediated by cGMP and are based upon multiple mechanisms including vasodilation, inhibition of renal sodium reabsorption, and inhibition of the renin-angiotensin-aldosterone system (Bestle M H et al., *Am J Physiol,* 276:R684-95 (1999)).

Ularitide is demonstrated to have a beneficial effect in CHF and acute decompensated heart failure (ADHF). In patients with CHF, urodilatin infusions for hours enhance natriuresis and diuresis and decrease central venous pressure without neurohumoral activation or adverse drug reactions (Elsner D et al., *Am Heart J,* 129:766-73 (I 995)). In addition, ularitide bolus injections to patients with ADHF stimulate diuresis and natriuresis and strongly reduce pulmonary capillary wedge pressure (PCWP) and systemic vascular resistance (SVR) (Kentsch M, et al., Eur J Clin Invest, 22:662-9 (1992)). These effects are more pronounced than those induced by equal doses of atrial natriuretic peptide (ANP) (Kentsch M, et al., *Eur J Clin Invest,* 22:662-9 (1992)).

The present study was undertaken to determine hemodynamic and neurohumoral effects as well as to assess the safety profile of continuous 24-hour infusions of different ularitide doses in patients with ADHF.

Methods

Study Design

This double-blind, placebo-controlled, ascending-dose study in patients with symptomatic ADHF was performed in 2 centers. For safety reasons, patients were randomly assigned to 3 ularitide-dose groups (7.5, 15, and 30 ng/(kg·min); CardioPep Pharma GmbH, Hannover, Germany) in ascending order, beginning with 7.5 ng/(kg·min). In each dose group, 6 patients were treated with ularitide and 2 patients with placebo.

All patients received their basal cardiovascular medication. During a 5-hour period (beginning 3 hours before the start of study drug infusion), phosphodiesterase inhibitors and IV administration of diuretics, angiotensin-converting enzyme (ACE) inhibitors, arid nitrates were only given if needed. Ongoing dobutamine/dopamine infusions were allowed to continue at a constant dose during this 5-hour period.

Administration of Study Drug

Ularitide (CardioPep Pharma GmbH), supplied as 1 mg of lyophilized powder containing 10 mg mannitol in glass vials, was reconstituted and further diluted with aqueous solution of 0.9% NaCl to the appropriate concentration of each dose group. Placebo vials contained 10 mg mannitol only. Placebo patients received an infusion solution containing 80 mg mannitol per 100 mL. For ularitide dosing, an infusion solution containing ularitide and 80 mg mannitol per 100 mL was used. The medication vials as well as the prepared infusion solution could not be distinguished by the study personnel.

All procedures complied with the Declaration of Helsinki institutional guidelines and were approved by the institutional review board of the Ethics Committee of the "Landesarztekammer Hessen," Frankfurt, Germany.

Patient Population

Twenty-four white patients (18 men and 6 women, mean age 66±12 years) with ADHF (New York Heart Association classes III-IV, cardiac index [CI] 1.91±0.34 L/min per square meter, PCWP 26±6 mm Hg, and right atrial pressure [RAP] 11±4 mm Hg), with dyspnea at rest or minimal physical activity requiring hospitalization, and who had right heart catheterization fulfilled all inclusion and exclusion criteria and were enrolled into the study. All patients gave written informed consent before entry into the study. Main exclusion criteria were systolic blood pressure ≤90 mm Hg, myocardial infarction within the previous 4 weeks, severe stenotic valvular diseases, and cardiogenic shock. Etiology of ADHF is given in Table 1.

Efficacy End Point Assessments

Hemodynamic parameters (PCWP, RAP, CI, and SVR) were determined by right heart catheterization using a Swan-Ganz thermodilution catheter. Stability of hemodynamic measurements was ensured as follows: cardiac output measurements for determination of CI at −60 minutes, −30 minutes, and before dosing were not allowed to vary ≥15%. Hemodynamics were then measured at 6 and 24 hours of dosing as well as 6 hours after end of dosing (30 hours).

Safety End Point Assessments

Enrolled hospitalized patients were monitored for blood pressure, heart rate, and adverse events. When systolic blood pressure decreased to ≤90 mm Hg, confirmed by a control measurement, the infusion was interrupted and recorded as an adverse event. Blood and urine were obtained from all patients before and at the end of the 24-hour study drug infusion for determination of safety laboratory parameters (clinical chemistry, hematology, and urinalysis). Fluid intake and urine output were documented. Fluid balance was calculated and adjusted according to cardiac filling pressures. A follow-up phone call was made on day for assessment of serious adverse events and vital status.

N-Terminal-Pro-Brain Natriuretic Peptide and cGMP

Venous blood was obtained for the determination of plasma concentrations of the following neurohumoral parameters: plasma N-terminal (NT) pro-brain natriuretic peptide (pro-BNP) was measured using the Elecsys 2010 pro-BNP sandwich immunoassay system with an analytical range extending from 20 to 35,000 pg/mL. For each individual patient, the change (delta NT-pro-BNP) over time was calculated. Plasma cGMP was measured using the IHF cGMP ELISA system (IHF GmbH, Hamburg, Germany) with an analytical range extending from 0.14 to 34.02 pmol/mL.

Dyspnea Assessment

Self-assessment of changes in dyspnea status was performed by all patients between baseline and the 6-hour time point after starting study drug infusion. Change in dyspnea status was assessed using the following 7-point categorical symptom response scale: markedly, moderately, or minimally improved; no change; or minimally, moderately, or markedly worsened. This scale was used recently in the pivotal VMAC trial. To avoid potential bias, dyspnea self-assessment at 6 hours was performed before hemodynamic measurements, and investigators were not allowed to discuss or assist the patients in completing the symptom evaluation.

Statistical Analysis

Data were double-key entered into an Excel 2000 sheet and then transferred to a SAS (version 8.2, SAS Institute, Cary N.C.) data base and verified. Data are given as mean±SD, ±SEM, or median with range (minimum-maximum). Statistical analysis was performed using 3-way analysis of variance including dose, center, and time effects. For baseline comparisons Dunnett t test was used. cGMP data were analyzed using analysis of variance followed by Dunnett posttests. P values ≤0.05 were considered to be statistically significant. Statistical analysis was performed in an exploratory sense; therefore, significance levels were not adjusted for multiple testing.

Results

Concomitant Cardiac Medication

Twenty-four patients were enrolled in 2 centers. Patients' basal cardiovascular medications included oral loop diuretics, thiazides, ACE inhibitors/angiotensin I blockers, β-blockers, spironolactone, and glycosides. Patients of the placebo and the 7.5 ng/(kg·min) groups more frequently received as basal medication hemodynamically acting nitrates and loop diuretics (Tables 1 and 3). IV dopamine infusions were ongoing at constant rates in 1 patient of the placebo and 1 in the 7.5 ng/(kg·min) groups (Table 1).

Hemodynamic Effects

At baseline, patient PCWP values were pathologically elevated in all treatment groups. At 6 hours, PCWP had significantly decreased in the 30 ng/(kg·min) ularitide group compared with placebo (P<0.05, FIG. 1) and in both the 15 and 30 ng/(kg·min) groups compared with 7.5 ng/(kg·min) (P<0.05, FIG. 1). After 24 hours of infusion, PCWP was still significantly decreased below baseline values in the 30 ng/(kg·min) group (P<0.05, FIG. 1). By 6 hours after discontinuation of infusion (at 30 hours FIG. 1), PCWP had essentially returned to pretreatment values in all groups. There was no "rebound effect," meaning an increase of PCWP to values higher than pretreatment levels, in any of the ularitide groups.

Figure 1B:
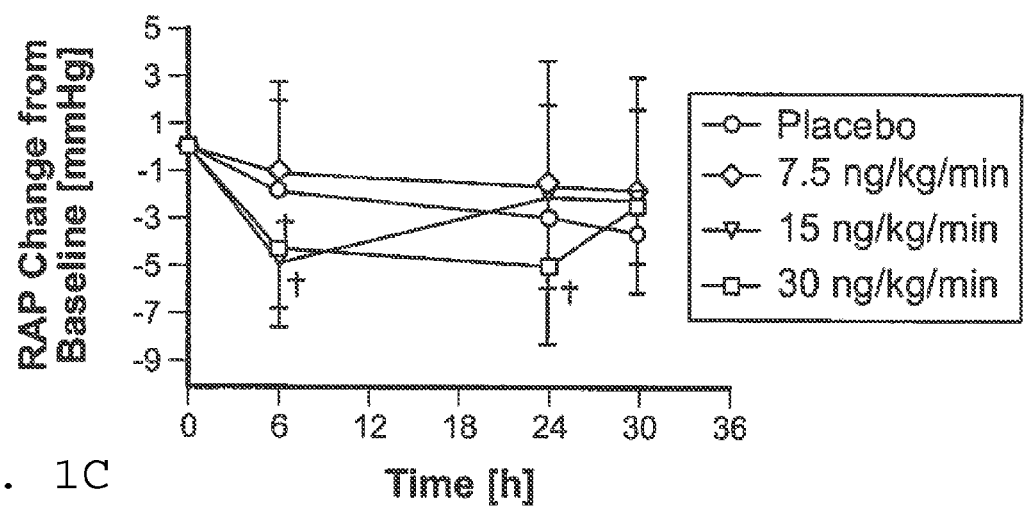
FIG. 1B: Graphical depiction of changes from baseline of RAP, during placebo or ularitide infusion, and after discontinuation of infusion. Values are mean±SD, n=6, *P<0.05 versus placebo, † P<0.05 versus baseline.
Figure 1C:
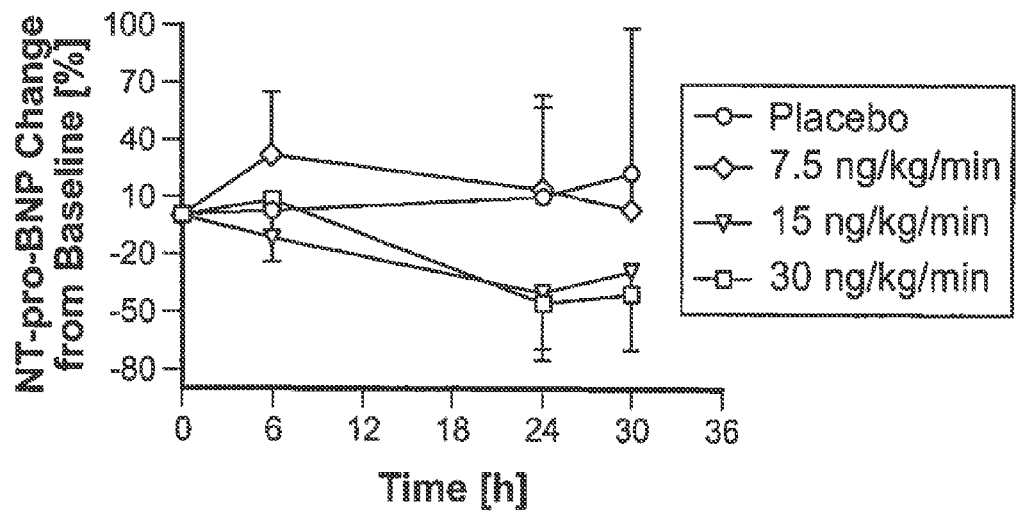
FIG. 1C: Graphical depiction of changes from baseline of NT-pro-BNP, during placebo or ularitide infusion, and after discontinuation of infusion. Values are mean±SD, n=6, *P<0.05 versus placebo, † P<0.05 versus baseline.
Figure 3:
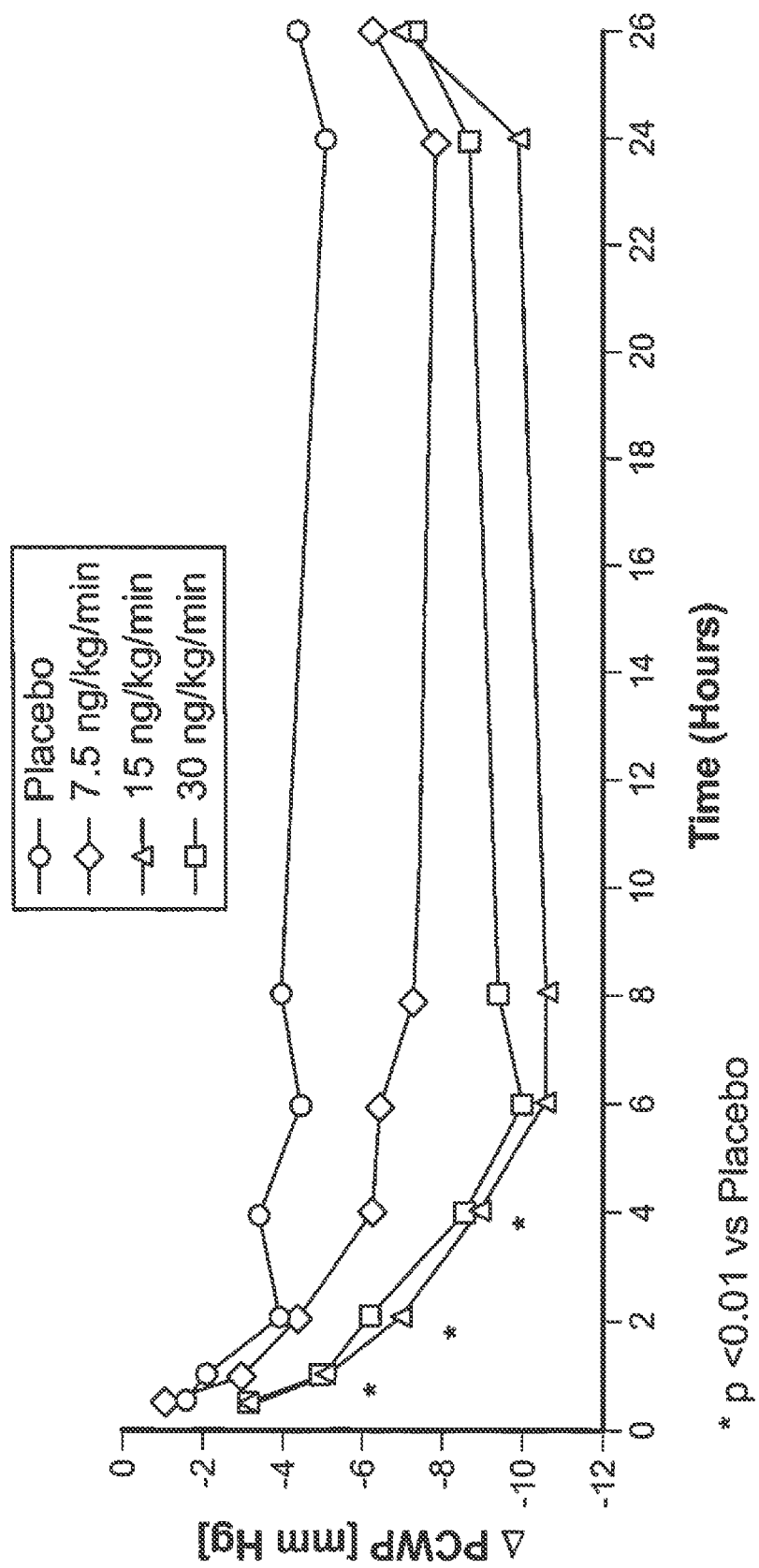
FIG. 3: Changes in pulmonary capillary wedge pressure (PCWP).

PCWP also decreased in the placebo group compared with baseline values at 24 and 30 hours (P<0.05, FIG. 1).

At baseline, RAP was also markedly elevated in all groups. Then at 6 hours, 15 and 30 ng/(kg·min) ularitide had significantly decreased RAP compared with baseline (FIG. 1) (P<0.05). Furthermore, at 24 hours, 30 ng/(kg·min) ularitide still significantly decreased RAP compared with baseline (FIG. 1) (P<0.05). At the 24-hour time point, in the 15 ng/(kg·min) group, RAP did not remain decreased and had returned to near baseline values.

At baseline, SVR was elevated, and CI was diminished in all treatment groups. In contrast to placebo and the lower dose ularitide groups, at 6 hours, 30 ng/(kg·min) ularitide tended to decrease SVR and to slightly increase CI (Table 2).

At 6 hours, compared with baseline, changes in systolic blood pressures were <5 mm Hg in the 7.5 ng/(kg·min) group (Table 2). In contrast, systolic blood pressure dropped in the placebo and 15 ng/(kg·min) ularitide groups, whereas it was significantly decreased in the 30 ng/(kg·min) group at 6 hours compared with baseline and with the 7.5 ng/(kg·min) ularitide group. Diastolic blood pressures only marginally decreased in the placebo and 7.5, and 15 ngl (kg min) ularitide groups. However, in the 30 ng/(kg min) ularitide group, diastolic blood pressure was decreased by approximately 10 nun Hg at 6 and 24 hours compared with baseline (Table 2). Heart rate did not change appreciably during ularitide infusion (Table 2).

Dyspnea Assessment

After 6 hours of study drug infusion, all 6 patients from each of the 4 respective treatment groups performed their self-assessment compared with baseline. Neither placebo, nor any patient from the 3 different ularitide groups reported a worsening of their status. No change of dyspnea was reported by 2, 1, and 2 patients from the 7.5, 15, and 30 ng/(kg·min) ularitide groups, respectively. A minimally better status was reported by all 6 placebo-treated patients, and 2, 1, and 1 patient from the 7.5, 15, and 30 ng/(kg·min) ularitide groups. Two, 3, and 2 patients from the 7.5, 15, and 30 ng/(kg min) ularitide groups felt moderately better, and 1 patient in each of the 15 and 30 ng/(kg·min) ularitide groups reported feeling markedly better. None of the patients reported a worsening of dyspnea.

Renal Effects and Use of Diuretics

Urine output did not significantly differ among the placebo and 7.5, 15, and 30 ng/(kg·min) groups (Table 2). However, loop diuretics were given more frequently in the placebo and the 7.5 ng/(kg·min) compared with the higher ularitide-dose groups (Table 3). Furthermore, the dosage of loop diuretics during study drug infusion was highest in the placebo group. Natriuresis was not measured; however, serum sodium levels did not change in the placebo and 7.5 and 15 ng/(kg·min) ularitide groups, but decreased in the 30 ng/(kg·min) ularitide group (Table 2). Although serum creatinine showed an increase in the 7.5 ng/(kg·min) ularitide group, decreases were seen in the 15 and 30 ng/(kg·min) ularitide groups as well as in the placebo groups. In contrast to the placebo and ularitide-treated (7.5 ng/[kg·min]) patients where the creatinine excretion decreased, there was a steep increase of creatinine excretion in the 15 and 30 ng/(kg·min) ularitide-treated patients (see Table 2).

Neurohumoral Parameters

Delta NT-pro-BNP.

At baseline, individual NT-pro-BNP levels were pathologically elevated. The median value was 5292 (range 691-29557) pg/mL. During the 24-hour infusion period, NT-pro-BNP levels did not change in the placebo, whereas they tended to increase in the 7.5 ng/(kg·min) ularitide group. In contrast, 15 and 30 ng/(kg·min) ularitide reduced NT-pro-BNP levels at 24 hours compared with baseline (FIG. 1).

cGMP.

At baseline, individual cGMP levels were not significantly different. The mean value was $13.5 \pm 2.0$ (SEM; N=24, range 0.51-51.5) pmol/mL. During the 24-hour infusion period, cGMP plasma levels did not change in the placebo group, but rose dose dependently and time-dependently. From 1 to 12 hours after start of dosing, plasma cGMP levels of the 15 and 30 ng/(kg·min) ularitide groups were significantly increased from baseline ($P \leq 05$ and 0.01). Also, the cGMP values of the 15 and 30 ng/(kg·min) groups were significantly higher than those of the placebo group from 1 to 12 hours after infusion start ($P \leq 05$).

Safety.

All 24 patients completed the treatment period, and no patient was prematurely withdrawn. One placebo patient died 8 days after end-of-study drug infusion. Another patient (7.5 ng/[kg·min] ularitide) died 20 days after end of dosing. A relationship with the study drug was considered unlikely.

During dosing, hypotension defined as decreases in systolic blood pressure to values ≤90 mm Hg occurred in 1 of 6 patients receiving 7.5 ng/(kg min), and in 2 of 6 patients receiving 30 ng/(kg min) ularitide. In 2 patients, study drug infusions were interrupted for 1 hour. All hypotensions were asymptomatic and completely resolved either spontaneously in 1 patient or during interruption of study drug in 2 other patients. No hypotensions were reported in the other treatment groups. During ularitide infusion of any dose, no significant changes in electrocardiographic findings were observed, nor did drug-related clinically relevant changes in safety laboratory parameters occur. Total number of patients with adverse events (AEs) in each group (placebo, 3; 7.5 ng/[kg·min], 5; 15 ng/[kg·min], 2; and 30 ng/[kg·min], 4) and total number of AEs in each group (placebo, 12; 7.5 ng/[kg·min], 12; 15 ng/[kg·min], 5; 30 ng/[kg·min], 15) were not significantly different.

Discussion

In this study, 24-hour infusions of ascending ularitide doses resulted in beneficial hemodynamic and neurohumoral effects in patients with ADHF.

Ularitide in a dose of 30 ng/(kg·min) caused substantial decrease in PCWP and RAP compared with placebo at 6 hours, whereas in the 7.5 ng/(kg·min) group, no effect of ularitide was observed. Urodilatin exerts vasodilatory effects (Bestle M H et al., *Am J Physiol,* 276:R684-95 (1999)). Therefore, decreased cardiac filling pressures most likely resulted from vasodilation, supporting ularitide's mode of action as a vasodilator. In contrast, PCWP also decreased in the placebo group compared with baseline values. However, this effect may have been caused by the higher use in dose and frequency of concomitant application of oral vasodilating nitrates and loop diuretics in the placebo compared with the ularitide groups. In patients with CHF, loop diuretics have vasodilatory properties on large vessels resulting in reductions of PCWP. The more pronounced RAP and PCWP reductions observed in both high urodilatin-dose groups clearly support the beneficial effects of ularitide in ADHF. These hemodynamic effects in the present study are compatible with those reported in a previous study where ularitide bolus injections in ADHF patients induced sustained reductions of PCWP and SVR accompanied by a steep increase in cGMP (Kentsch M, et al., *Eur J Clin Invest,* 22:662-9 (1992)).

At the 24-hour time point of study drug infusion, ularitide's effect on PCWP appeared to be attenuated in the 30 ng/(kg·min) dose group but not in the 15 ng/(kg·min) group. In addition, that ularitide's effect on RAP appeared to be attenuated in the 15 ng/(kg·min) group but not in the 30 ng/(kg·min) group may be supporting an attenuation of ularitide's effects. In parallel, plasma cGMP levels increased in the 15 and 30 ng/(kg·min) groups with both peaking at 6 hours followed by a decrease which still tended to remain above baseline levels at 24 hours. However, in patients with chronic heart failure, prolonged ANP infusions after an increase also led to a decrease in plasma cGMP levels (Munzel T et al., *Circulation*, 83:191-201 (1991)). Decrease in cGMP, despite ongoing natriuretic peptide infusion, may also be a result of decreased BNP levels, changes in nitric oxide production (Takahashi Metal., *Jpn Heart J*, 44:713-24 (2003)), or increased activation of serum phosphodiesterases. Therefore, whether a decrease of cGMP reflects a lesser binding of ularitide to the receptor over time still needs to be clarified. If so, one would have also expected to see a parallel decrease in both PCWP and RAP, which was not the case. Furthermore, both PCWP and RAP were still below baseline values at 24 hours. In addition, at high doses, nesiritide exerted similar weaning of the PCWP effects in a smaller study (Mills R M et al., *J Am Colt Cardiol*, 34:155-62 (1999)), which was not confirmed in the larger pivotal VMAC trial (Publication Committee for the VMAC Investigators, *JAMA*, 287:1531-40 (2002)). Therefore, larger trials need to demonstrate the effect of increasing ularitide concentrations over time on pharmacodynamic parameters.

The most prominent symptom for patients with ADHF is dyspnea. Therefore, patients themselves performed dyspnea self-assessments using a 7-point scale as described earlier in the pivotal VMAC trial (Cowie M R et al., *Eur. Heart J*, 24:1710-8 (2003)). Compared with placebo, patients receiving the highest doses of ularitide tended to report a stronger improvement of dyspnea after 6 hours of infusion. Patient number may limit the interpretation, in particular of subjective data. However, these data are in accordance with those also reported for BNP in the VMAC trial when nesiritide significantly improved the patient's self-evaluation of dyspnea compared with placebo (Publication Committee for the VMAC Investigators, *JAMA*, 287:1531-40 (2002)).

At baseline, plasma NT-pro-BNP concentrations were increased followed by a ularitide-induced decrease in the 2 higher groups at 24 hours. The maximum change in PCWP at 6 hours correlated significantly with the percent change of NT-pro-BNP from baseline at 24 hours. Because 24 hours was the first measurement after 6 hours, one cannot exclude whether a reduction of the NT-pro-BNP levels earlier than 24 hours already occurred. However, PCWP by increasing ventricular wall tension is an important stimulus for NT-pro-BNP release. The mechanism by which NT-pro-BNP secretion is controlled includes the transcriptional level, usually requiring a longer term stimulus (Cowie M R et al., *Eur. Heart J*, 24:1710-8 (2003)). Therefore, abrupt reductions in right and left ventricular filling pressures may not directly result in a reduction of NT-pro-BNP. This is also supported by McCullough et al (McCullough P A et al., *Rev Cardiovasc Med*, A:72-80 (2003)) who stated that "the half-life of NT-pro-BNP is 120 minutes, suggesting that hemodynamic changes could be reflected by this test approximately every 12 hours."

Urodilatin is known to induce renal effects such as diuresis and natriuresis (Forssmann W et al., *Cardiovasc Res*, 51:450-62 (2001)). Among the 4 treatment groups, there was no significant difference in the urine output over 24 hours. However, all 6 patients in the placebo group and 5 of 6 patients in the low-dose ularitide group received loop diuretics during infusion of trial medication. In contrast, only 3 patients of the 2 higher ularitide-dose groups received loop diuretics, possibly supporting ularitide's diuretic effects. Serum creatinine levels among the groups were not significantly different. In contrast, decrease in serum sodium in the 30-ng group and increase in urinary creatinine in both the 15- and 30-ng groups may support ularitide's effects on renal function. However, larger trials are needed to confirm these data. Nesiritide, which is approved for the treatment of ADHF in the United States, was recently shown not to improve renal function in patients with CHF (Wang D J et al., *Circulation*, 110:1620-5 (2004)). However, renal function has an impact on prognosis of congestive heart failure (Akhter M W et al., *Am J Cardiol*, 94:957-60 (2004)). Therefore, besides improvement of hemodynamics, improvement of renal function may be an important target for effectively treating ADHF by the renal natriuretic peptide ularitide.

ANP (carperitide), another natriuretic peptide, is also approved for ADHF (in Japan). Although no comparative studies have been made so far between ularitide and nesiritide, there is one report comparing ularitide with ANP bolus application in DHF patients (Kentsch M, et al., *Eur J Clin Invest*, 22:662-9 (1992)). These authors reported more pronounced and longer lasting hemodynamic effects of ularitide compared with those induced by ANP (Kentsch M, et al., *Eur J Clin Invest*, 22:662-9 (1992)). One explanation for the stronger pharmacodynamic effects of urodilatin is urodilatin's higher resistance against enzymatic degradation by the neutral metalloendoprotease EC24.11 compared with ANP (Gagelmann M et al., *FEBS Lett*, 233:249-54 (1988)).

Hypotensive episodes occurred after infusions of nesiritide and ANP in normal subjects and in patients with CHF and ADHF (Hobbs R E et al., *Am J Cardiol*, 78:896-901 (1996); Northridge D B et al., *Herz*, 16:92-101 (1991)). Comparably, in the present study, hypotension was reported to be asymptomatic and transient. These effects were observed in the 7.5 and 30 ng/(kg·min) ularitide groups and completely resolved. However, in the placebo group also, systolic blood pressure decreased (Table 2), possibly because of nitrate co-medication (Table 3). During dosing, no clinically significant drug-related changes in safety laboratory parameters occurred in either group, and no serious drug reactions occurred in any patient. In 1 patient with CHF, ularitide incidentally caused bradycardia and hypotension (Kentsch M et al., *Eur J Clin Invest*, 25:281-3 (1995)). However, in the present study, no bradycardia or tachycardia occurred, thus supporting the lack of proarrhythmic potential of natriuretic peptides (Burger A J, et al., *Am Heart J*, 144:1102-8 (2002)).

The authors are aware of the limitations of the study as a result of the small sample size and that further trials are still needed to confirm the data in a larger number of patients. Although total number of serious AEs (1 death in the placebo and 1 in the 7.5-ng group) and AEs are equally distributed among the serum and the placebo groups, more data are needed to evaluate the safety profile of this drug.

The present study underlines that ularitide infusions at the 2 higher doses may result in beneficial hemodynamic effects associated with improvement of dyspnea, an increase in plasma cGMP levels, and a decrease in plasma NT-pro-BNP levels.

This study was supported by CardioPep Pharma GmbH and in part by the Ministry of Economics of the State of Lower Saxony, Research & Development grant (Az. 203.19-32329-5-405).

Example 2

Ularitide is a natriuretic peptide that is synthesized in the kidneys. Its main pharmacological actions include vasodilation, diuresis, and natriuresis. The aim of this double-blind, randomized, placebo-controlled phase II dose-finding study (SIRIUS II) was to establish a safe and efficacious dosage of ularitide in patients with acute decompensated heart failure (ADHF).

A total of 221 patients with ADHF (inclusion criteria: cardiac index ≤2.5 l/min per m2, mean pulmonary capillary wedge pressure (PCWP) ≥18 mm Hg) were randomized to receive an intravenous infusion over 24 h of ularitide (7.5, 15, or 30 ng/kg/min) or placebo. Primary endpoints were reduction of PCWP and improvement of patients dyspnea, both at 6 h. Ularitide reduced PCWP (p<0.05) and improved dyspnea score (p<0.05) in all three dose groups compared to placebo. Serum creatinine levels did not increase during and after Ularitide treatment when compared to placebo:

|  | Serum Creatinine [mg/dl] | | | |
| --- | --- | --- | --- | --- |
|  | Placebo | 7.5 ng/kg/min | 15 ng/kg/min | 30 ng/kg/min |
| Baseline (mean ± std dev) | 110.5 ± 36.8 | 104.8 ± 32.7 | 109.1 ± 30.8 | 107.8 ± 32.3 |
| 24 hours | 110.1 ± 30.5 | 105.4 ± 36.2 | 106.9 ± 29.0 | 112.6 ± 43.5 |
| 148 hours | 120.6 ± 42.2 | 116.8 ± 43.0 | 116.6 ± 41.9 | 121.7 ± 47.7 |
| 72 hours | 114.8 ± 38.2 | 117.3 ± 51.5 | 114.5 ± 39.1 | 117.9 ± 41.6 |

30-day mortality rate was higher in the placebo compared with the three ularitide groups: 13.2% in the placebo and 3.3% (p=0.080, compared to placebo), 3.8% (p=0.16), and 1.8% (p=0.029) in the 7.5, 15 and 30 ng/kg/min groups, respectively. All three doses of ularitide were well-tolerated. Main adverse events were asymptomatic blood pressure decrease/hypotension, most frequently reported in the 30 ng/kg/min group.

Ularitide infusions for 24 h resulted in beneficial hemodynamic effects that were associated with dyspnea symptom reduction.

Example 3

Ularitide is a synthetic form of urodilatin, a natriuretic peptide secreted by the kidney with natriuretic, diuretic, vasodilating, and hemodynamic effects that offers promise for the management of acute decompensated heart failure (ADHF).

The purpose of this study was to assess the efficacy and safety of ularitide when added to standard therapy in the treatment of patients with ADHF.

This was a phase 2 randomized, double-blind, placebo-controlled trial involving 221 hospitalized patients with ADHF (cardiac index [CI]≤2.5 L/min/m$^2$; mean pulmonary capillary wedge pressure [PCWP]≥18 mm Hg) conducted at 19 study centers in Europe and Russia between February 2003 and October 2004.

Patients were randomized to receive either placebo (n=53) or ularitide at 7.5 ng/kg/min (n=60), 15 ng/kg/min (n=53), or 30 ng/kg/min (n=55) as a 24-hour continuous infusion. Co-primary efficacy endpoints included PCWP and dyspnea score. Additional measures included hemodynamics, length of hospitalization, mortality, and safety. See FIGS. 2-17.

At 6 hours, ularitide demonstrated a significant decrease in PCWP (Δ±SD/mm Hg): placebo, −4.4±6.1; ularitide 7.5 ng/kg/min, −6.5±7.2 (P<0.05); 15 ng/kg/min, −10.5±6.3 (P<0.01); 30 ng/kg/min, −10.1±5.7 (P<0.01), and improved dyspnea score (P=0.05). Ularitide dose-dependently reduced systemic vascular resistance (Δ±SD/dyn·sec·cm$^{-5}$): placebo, −140±315; 7.5 ng/kg/min, −184±373; 15 ng/kg/min, −375±444 (P<0.01); 30 ng/kg/min, −445±428 (P<0.01), increasing CI for the 15 and 30 ng/kg/min groups (P<0.05). Systolic blood pressure decreased dose-dependently. Heart rate and serum creatinine were unchanged through day 3. Most frequently reported drug-related AEs through day 3 in all ularitide groups were blood pressure decrease (5.4%), hypotension (5.4%), sweating (4.2%), and dizziness (3.0%). The mortality rate (day 30) was significantly higher for the placebo group compared to the 30 ng/kg/min ularitide group (13.2% vs 1.8%, P<0.05).

Ularitide lowered cardiac filling pressures, improved dyspnea, reduced mortality, and did not compromise renal function in ADHF patients. These results indicate that ularitide is useful in the management of ADHF patients when added to standard therapy.

Introduction

Heart failure is a major, expanding public health problem. Lifetime risk of heart failure is ~20% in both men and women, and over 550,000 cases are diagnosed annually in the US. Heart failure prognosis is generally poor: the 5-year survival rate for patients with mild to moderate disease is ~50%, and half of patients with severe heart failure die within 2 years. Heart failure is also the most common cause for the hospitalization of elderly patients, with hospitalization alone accounting for ~60% of the cost of treatment.

Ularitide is a synthetic form of urodilatin, a natriuretic peptide hormone secreted by the kidney. The natriuretic peptide family is comprised of peptides secreted by various organs, including atrial natriuretic peptide (ANP) and brain natriuretic peptide (BNP), which are secreted by the heart. These molecules regulate vascular and renal homeostasis, increase vasodilation and urinary sodium, chloride, and volume excretion, and decrease neurohumoral vasoconstrictor activation. In contrast to ANP and BNP, endogenous urodilatin is synthesized in renal distal tubular cells. Following luminal secretion, urodilatin binds natriuretic peptide type A, B and C receptors in the inner medullary collecting duct, regulating renal sodium and water excretion.

The immediate clinical goal in the management of acute decompensated heart failure (ADHF) patients is to stabilize the patients' hemodynamics and provide symptom relief. Therapeutic options include diuretics, vasodilators, and positive inotropic agents. However, each of these options is associated with clinical limitations, including deleterious effects on kidney and long-term survival. Thus, the search for agents that improve ADHF signs and symptoms and preserve renal function without increasing mortality risk has been an area of ongoing research.

Ularitide has previously demonstrated beneficial effects in congestive heart failure (CHF) and ADHF. Bolus injections in ADHF patients stimulated diuresis and natriuresis, and significantly reduced pulmonary capillary wedge pressure (PCWP) and systemic vascular resistance (SVR). These effects were more pronounced than those induced by equal doses of ANP. Further, in the SIRIUS I study, 24-hour ularitide infusions reduced PCWP and tended to improve dyspnea. This phase 2 study, SIRIUS II, evaluated the hemodynamic and clinical effects of intravenous ularitide when added to standard therapy in hospitalized ADHF patients with dyspnea at rest or minimal physical activity.

Natriuretic peptides such as urodilatin, particularly its synthetic version (also known as ularitide), have been used for treating heart failure patients. The present inventors discovered that a continuous infusion of a natriuretic peptide (e.g., urodilatin) at a relatively low concentration over a time period (e.g., from about 24 hours to about 120 hours) provides superior efficacy for treating heart failure, particularly acute decompensated heart failure. Such lower dose of natriuretic peptide allows the treatment method to achieve the desired results while avoiding adverse side effects such as potential harmful effects to the kidney.

Methods

Study Design

This randomized, double-blind, placebo-controlled study in patients with ADHF was performed in 13 German, 2 Serbian, and 4 Russian centers. Patients were randomized to 3 ularitide dose groups (7.5, 15, and 30 ng/kg/min) or placebo (FIG. 2). All patients received standard care cardiovascular medication. During a 5-hour period (beginning 3 hours prior to initiating study drug infusion), IV diuretics, angiotensin-converting enzyme (ACE) inhibitors, vasoactive drugs and phosphodiesterase (PDE) inhibitors and new intravenous (IV) administration of dopamine/dobutamine, were excluded. Ongoing dobutamine/dopamine infusions were continued at a constant dose during this 5-hour period.

Hemodynamic parameters such as PCWP, right atrial pressure (RAP), and cardiac output (CO) were measured before, during, and 2 hours after the end of the infusion. Before, at 6 hours, and at 24 hours after the start of infusion, an assessment of dyspnea was performed independently by the patient and the investigator. Blood pressure, heart rate, and ECG were closely monitored throughout the infusion. If the systolic blood pressure decreased to ≤80 nun Hg or decreased by >50 mm Hg from a pre-existing hypertensive state, and the value was confirmed within 5 minutes, the infusion was stopped for at least 1 hour and then restarted at the same dose. Adverse events (AEs) were recorded and serum creatinine levels were measured throughout the trial up to 3 days from the initiation of infusion. Serious adverse events and mortality were monitored through day 30.

Prior to and at the end of infusion, safety laboratory assessments (clinical chemistry, hematology, and urinalysis) were performed. At the end of the 30-day follow-up period, the investigator contacted each patient or the patient's family doctor to assess rehospitalization and mortality.

Administration of Study Drug

Ularitide (CardioPep Pharma GmbH, Hannover, Germany) supplied as 1 mg of lyophilized powder, containing 10 mg mannitol in glass vials, was reconstituted and further diluted with an aqueous solution of 0.9% NaCl as described elsewhere.

The study was conducted in accordance with the Declaration of Helsinki and its amendments and with Good Clinical Practice Guidelines, and in agreement with the local ethics committees.

Patient Population

Two-hundred and twenty-one Caucasian patients with ADHF and dyspnea (at rest or with minimal physical activity) requiring hospitalization were enrolled in the study. All patients gave written informed consent prior to entry into the study. Baseline hemodynamic measures were CI: mean of 1.9 L/min/m2; PCWP: mean of 25 mm Hg; ejection fraction <40%:95%. Among the different groups, median interval length from the time of hospitalization to the start of study drug infusion ranged from 2 to 3 days. All patients had right heart catheterization. Exclusion criteria included systolic blood pressure ≤90 mm Hg, myocardial infarction within the 4 weeks prior to study entry, severe stenotic valvular diseases, serum creatinine levels >2.5 mg/dL, and cardiogenic shock.

All patients who were randomized to treatment represented the safety population. For the intent-to-treat (ITT) analysis (220 patients), 1 patient from the 15 ng/kg/min ularitide group was excluded because of a short duration of infusion (20 minutes) and no valid follow-up data.

Efficacy Endpoint Assessments

The co-primary endpoints at 6 hours were: 1) change in PCWP compared to placebo, and 2) changes in the patient's self-assessed dyspnea score, conducted independently from the investigator, compared to placebo.

Hemodynamics

Hemodynamic parameters PCWP, RAP, and CO were determined by right heart catheterization using a 7F-Swan-Ganz thermodilution catheter. Stability of hemodynamic measurements was ensured as follows: CO measurements at −30 minutes and immediately before dosing were not allowed to vary by 15% or more. Hemodynamic parameters were then measured at +30 min, 1, 2, 4, 6, 8, and 24 hours of dosing as well as 2 hours after the end of dosing (26 hours). CI and SVR were calculated. Myocardial oxygen consumption ($MVO_2$) was calculated using the formula of Rooke and Feigl.

Patient-Assessed Dyspnea

Patient self-assessment of dyspnea was recorded by 7-point Likert scale (minimally, moderately, markedly worse; unchanged; minimally, moderately, markedly better) as described previously. Patient-assessed dyspnea was blinded to hemodynamic measurement.

Renal Parameters

Creatinine clearance ($CL_{CR}$) was estimated from serum creatinine using the. Cockroft-Gault equation:

$$CL_{CR}=[(140-\text{age in years})\times(\text{body weight in kg})]/(72\times \text{serum creatinine in mg/dL})$$

In women, the value is then multiplied by 0.85. This formula has been validated in several studies of CHF and renal dysfunction, but is used only if serum creatinine is measured by the Jaffé method.

Nt-proBNP

Venous blood was obtained for the determination of plasma concentrations of N-terminal-proBNP (NT-proBNP). NT-proBNP was measured using the Elecsys 2010 proBNP sandwich-immunoassay system (Roche Diagnostics, Basel, Switzerland) with an analytical range of 20 to 35,000 pg/mL.

Safety Endpoint Assessments

Enrolled patients were hospitalized and monitored for blood pressure, heart rate, ECG, and AEs. AEs were recorded through 72 hours. Serious adverse events and mortality were monitored through 30 days. If systolic blood pressure decreased to ≤80 mm Hg, confirmed by a control measurement within 5 minutes, the infusion was interrupted and this was recorded as an AE. Blood and urine samples were obtained from all patients prior to and at the end of the 24-hour study drug infusion for determination of safety laboratory parameters (clinical chemistry, hematology, and urinalysis). Fluid intake and urine output were documented. Fluid balance was calculated and adjusted according to cardiac filling pressures. A follow-up phone call was made on day 30 for assessment of serious adverse events (SAEs) and vital status.

Statistical Analysis

All efficacy and safety parameters were described and summarized by treatment group and time point (n, arithmetic mean, standard deviation, median, minimum, maximum).

The primary endpoint (i.e., the absolute change from baseline in PCWP after 6 hours) was evaluated by analysis of covariance (ANCOVA) including baseline as covariate, treatment, and center as factors as well as treatment-by-center interaction. If the overall F-test gave an indication of a difference between the means, hierarchical testing was performed comparing the active doses to placebo, starting with the highest dose (alpha=0.05) and stopping if one test was not significant. Due to the hierarchical test principle, all tests were performed at the local 5% level and no alpha-adjustment was necessary.

All active doses that showed a significant difference compared to placebo were then tested against each other. For all differences, 95% confidence intervals were calculated, estimating the variability by using the mean squared error of the ANOVA procedure. P-values were also derived for other parameters and time points of interest, using corresponding methods. These p-values can be interpreted as a descriptive measure of the strength of evidence, independent of the scale of measurement, but should not be interpreted as a statistical proof of any actual or assumed differences.

The dyspnea score was described by frequency tables in terms of counts and percentages. Data were analyzed by assessor and time point with a chi-square test taking into account the influence of the centers in the form of a Cochran-Mantel-Haenszel analysis.

Adverse events were coded using the MedDRA dictionary. The incidence of each adverse event (coded by preferred term) and the number and percentage of subjects experiencing each adverse event were determined within each treatment group.

Results
Patient Enrollment

Between February 2003 and October 2004, 221 patients were randomized (53 patients in the placebo group, 60 in the 7.5 ng/kg/min ularitide group, 53 in the 15 ng/kg/min ularitide group, and 55 in the 30 ng/kg/min ularitide group), of which 220 were treated with study drug over 24 hours. Out of the 221 patients (safety population), 220 were included in the ITT population.

Baseline Characteristics

For the 221 randomized patients, 173 (78.3%) were male. The mean study population age was 61 years. Demographic characteristics were comparable among the 4 treatment groups. There were no relevant differences in age, height, or weight. All subjects were Caucasian (Table 4).

Mean hemodynamics at baseline were comparable among the different groups with respect to CI, PCWP, and ejection fraction. Median NT-proBNP levels ranged from 2.64 to 3.52 pg/ml between treatment groups. Cardiovascular medical history was comparable for all 4 treatment groups. Most patients had ischemic cardiomyopathy (ICM) as the primary etiology of their CHF (47 to 57%) (Table 4). Main baseline medication consisted of diuretics, ACE inhibitors, beta blockers, digoxin, and nitrates (Table 5).

Hemodynamic Effects

At 6 hours, the primary endpoint, PCWP (FIG. 3), significantly decreased in all ularitide groups compared to placebo. The greatest decreases were observed in the 15 and 30 ng/kg/min groups (P<0.01), while there was a smaller but significant reduction in the 7.5 ng/kg/min group (P<0.05). In both the 15 and 30 ng/kg/min groups, PCWP was significantly reduced at 16 hours compared to the 7.5 ng/kg/min group (P<0.01). There was no difference between the 2 highest dose groups (P=0.930). The changes from baseline for the 15 and 30 ng/kg/min groups vs placebo showed significant differences (P<0.01) at 1 hour after onset of infusion, lasting until 24 hours, while for 7.5 ng/kg/min, these differences (P<0.01) were first evident at 4 hours, lasting until 24 hours (P<0.05) (Table 6).

At baseline, right atrial pressure (RAP) was markedly elevated in all groups. At 4 hours, the 7.5, 15, and 30 ng/kg/min ularitide treatment groups displayed decreased RAP compared to placebo (P<0.01) lasting until 24 hours for the 7.5 and 30 ng/kg/min ularitide groups (P<0.05) (Table 6). The mean decrease observed among the 15 ng/kg/min patients was twice that of the placebo group but not statistically larger.

Systemic vascular resistance (SVR) decreased 1 hour after start of dosing in the 15 and 30 ng/kg/min groups compared to placebo (P<0.01) lasting through 24 hours, except at 4 hours for the 15 ng/kg/min group (P>0.05) (Table 6).

The time course of SVR was mirrored by that of CI. For the 15 and 30 ng/kg/min ularitide groups, there was an increase of CI already evident at 1 hour following the start of infusion (P<0.01). Throughout the infusion period, and 2 hours after end of dosing, CI remained elevated in the 30 ng/kg/min group. Ularitide at 15 ng/kg/min increased CI similarly (P<0.05) at 6 hours (Table 6).

There was a dose-related decrease in systolic blood pressure during infusion (Table 6). At 4 hours, the 7.5, 15, and 30 ng/kg/min ularitide treatment groups demonstrated decreased systolic blood pressure by −6.9, −9.0, and −13.4 mm Hg, respectively. There was also a −5.8 mm Hg decrease in systolic blood pressure in the placebo group. The largest decreases occurred after approximately 6 hours, with only minimal changes at 24 hours. After the end of infusion, systolic blood pressure increased again in the 15 and 30 ng/kg/min ularitide groups. Mean arterial blood pressure (MAP) also decreased in a dose-related fashion. However, mean MAP did not drop below 80 mm Hg in any of the ularitide treatment groups. Heart rate did not change during ularitide infusion and was not different among the groups (data not shown).

Figure 4:
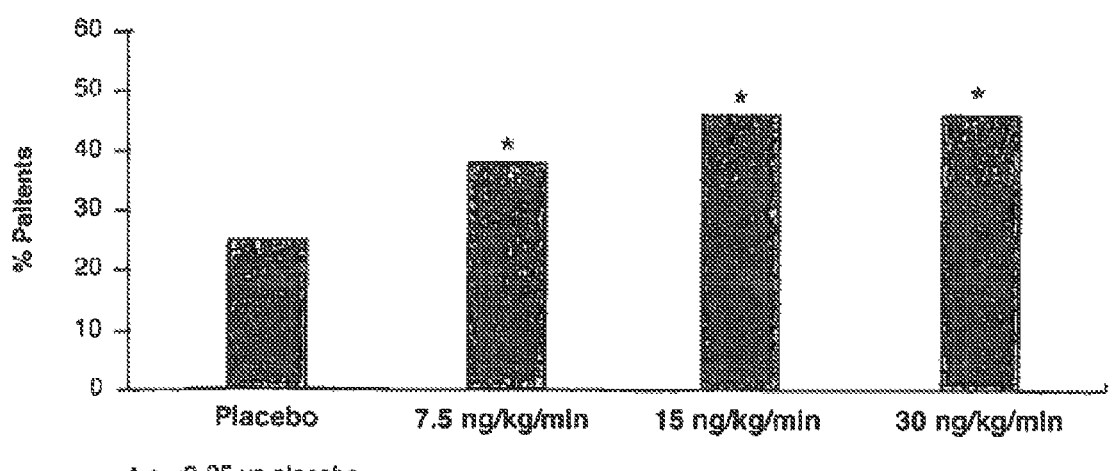
FIG. 4: Dyspnea improvement at 6 hours. Summarized patient assessments of "moderately better" or "markedly better." *P<0.05 vs placebo. **P<0.01 vs placebo.
Figure 5A:
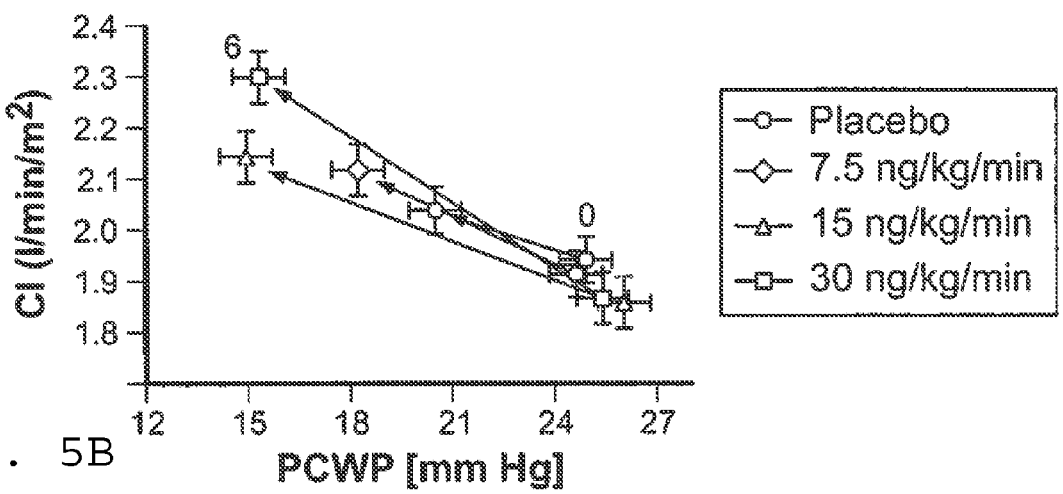
FIG. 5A: Graphical depiction of cardiac and hormonal parameters. Left ventricular pump function defined by the relationship between cardiac index (CI) and mean pulmonary capillary wedge pressure (PCWP).
Figure 5B:
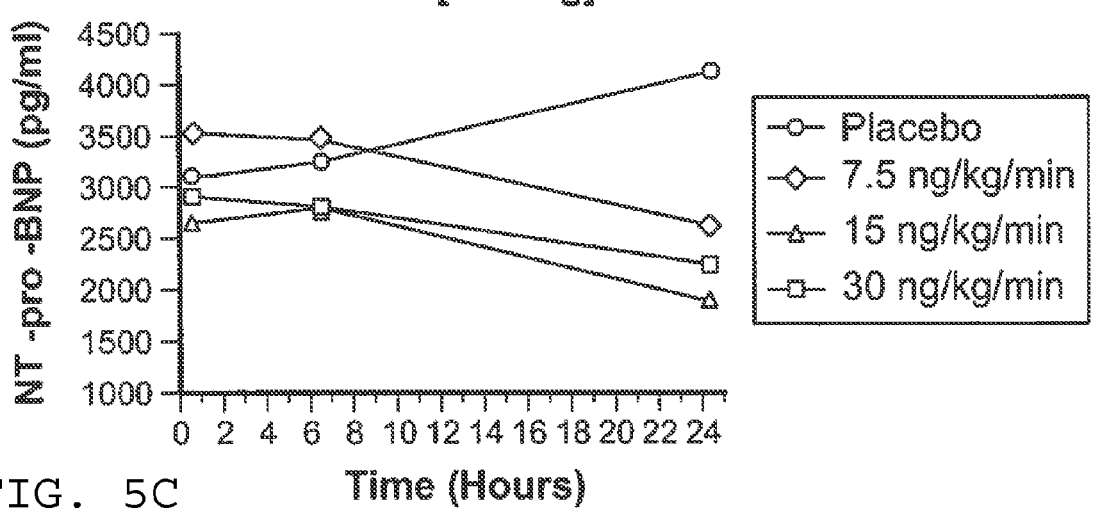
FIG. 5B: Graphical depiction of hormonal parameters. NT-pro-BNP, N-terminal pro BNP. *P<0.05 vs placebo. **P<0.01 vs placebo.
Figure 5C:
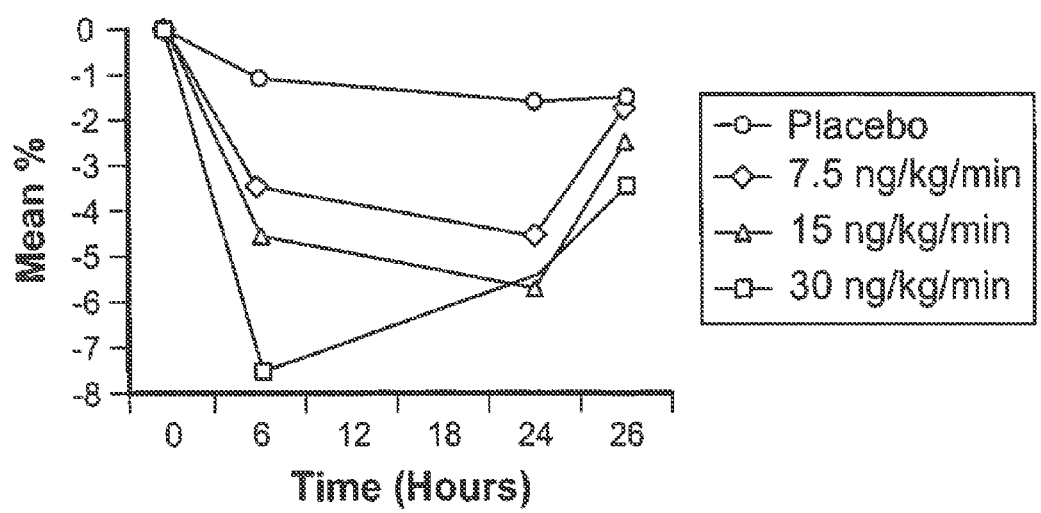
FIG. 5C: Graphical depiction of cardiac and hormonal parameters. Myocardial oxygen consumption.
Figure 6A:
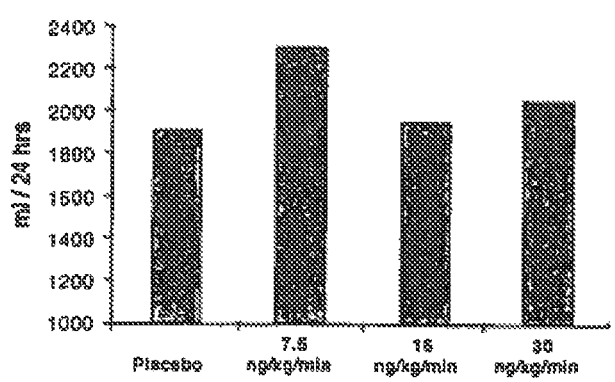
FIG. 6A: Graphical depiction of renal parameters. Urine output over 24 hours.
Figure 6B:
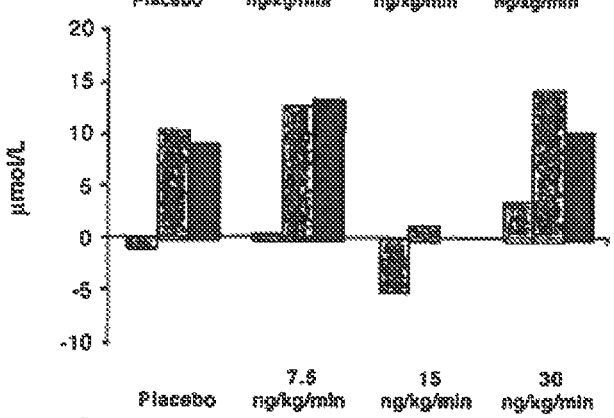
FIG. 6B: Graphical depiction of renal parameters. Changes in serum creatinine.
Figure 6C:
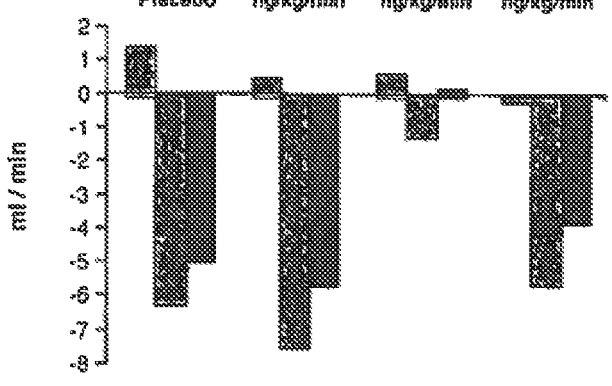
FIG. 6C: Graphical depiction of renal parameters. Changes in creatinine clearance.
Figure 6D:
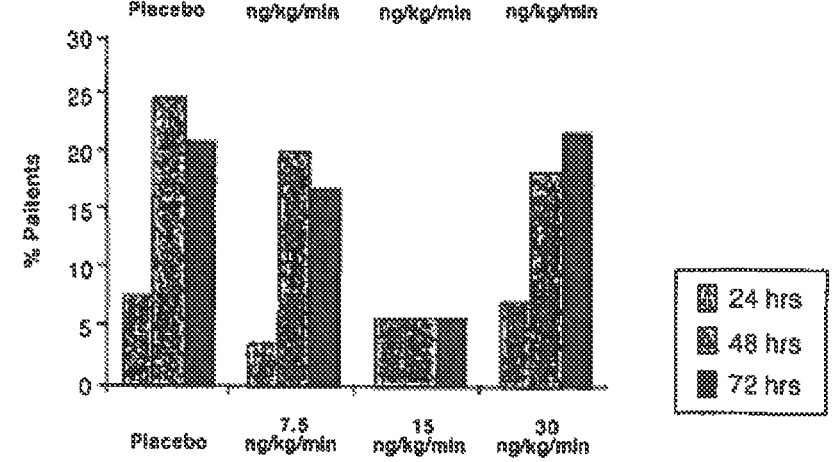
FIG. 6D: Graphical depiction of renal parameters. Total incidence of creatinine increases >25%.
Figure 7:
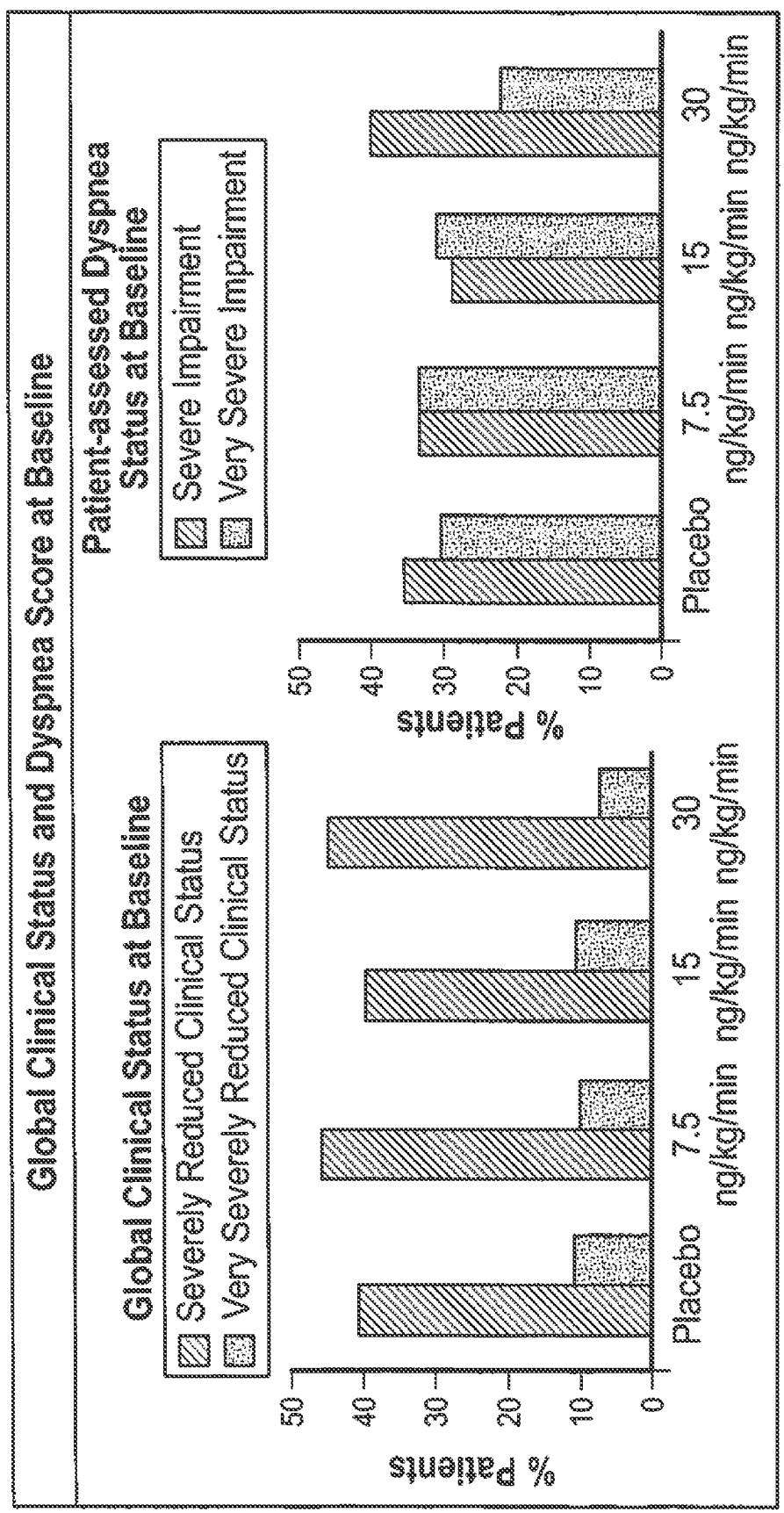
FIG. 7: Patient global clinical status and dyspnea score at baseline.
Figure 8:
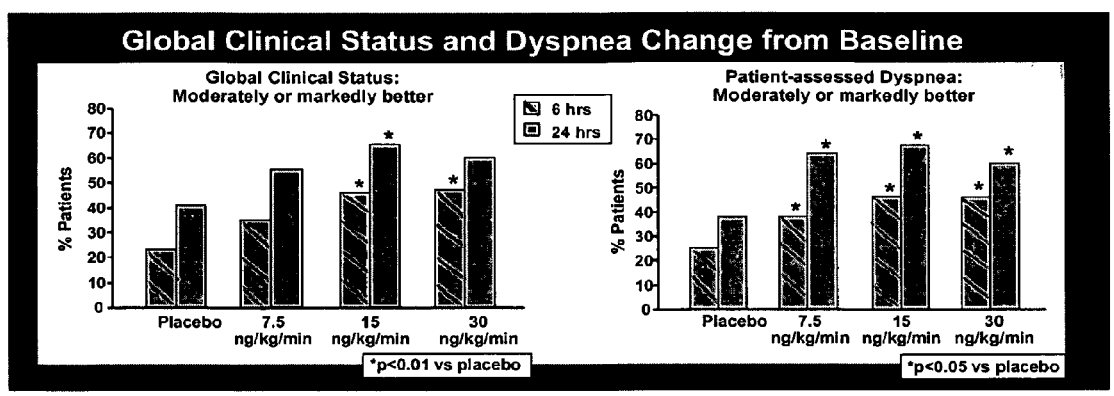
FIG. 8: Patient global clinical status and dyspnea change from baseline.
Figure 9:
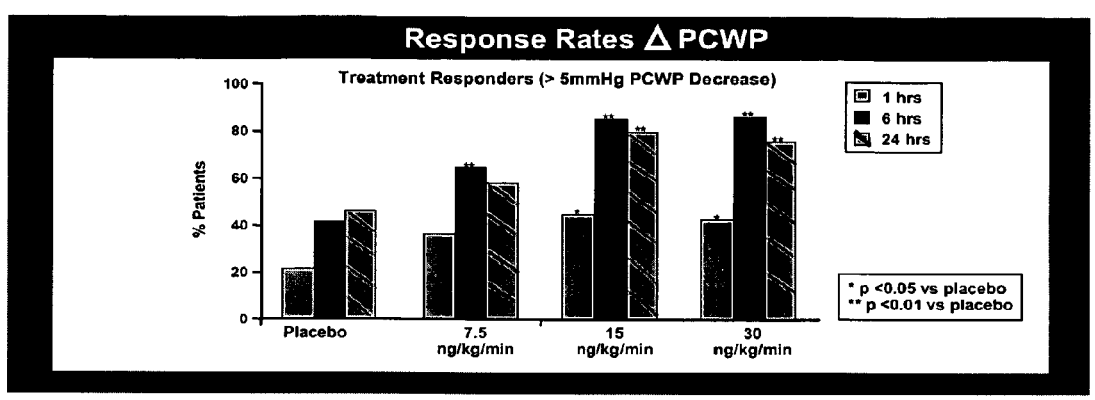
FIG. 9: Patient PCWP change in response to treatment.
Figure 10:
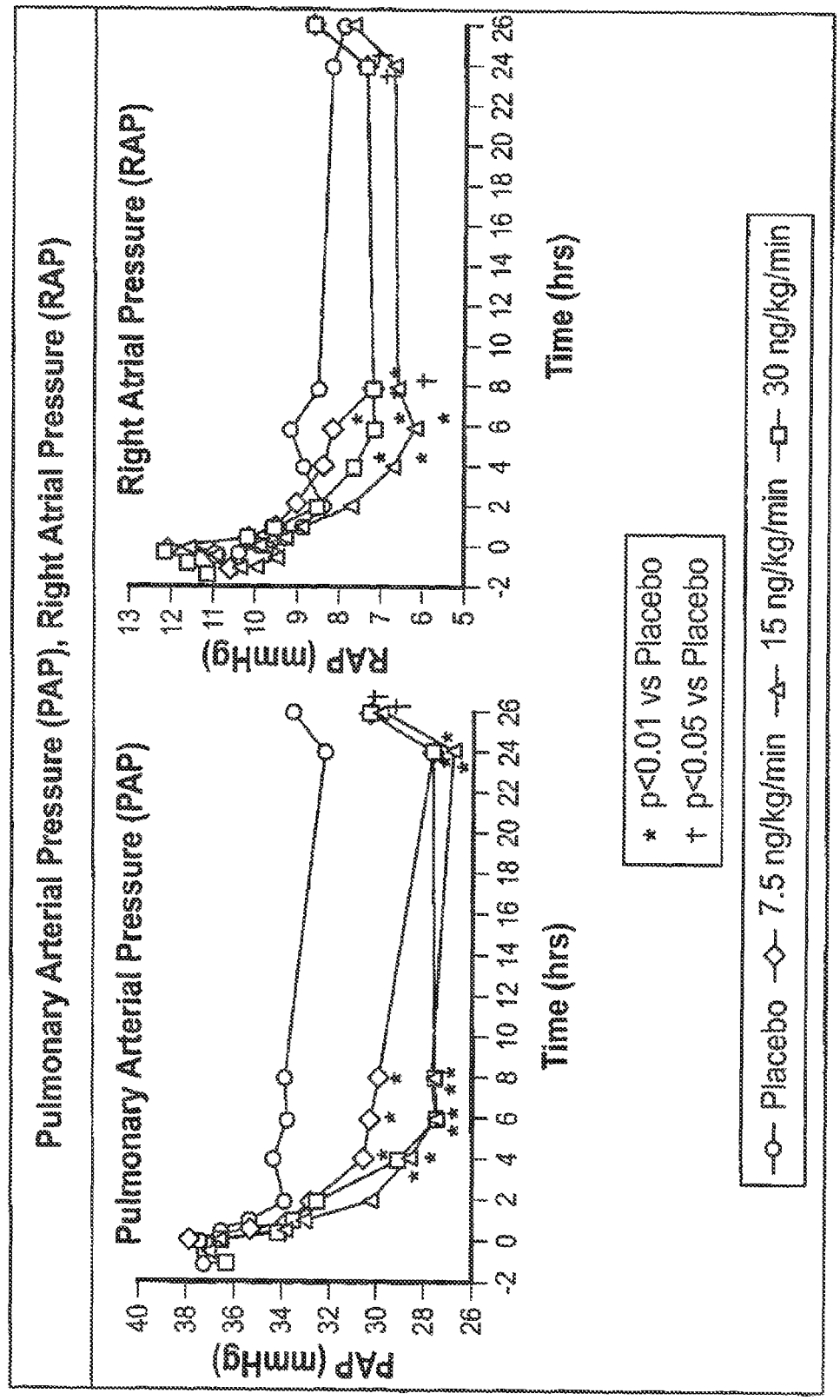
FIG. 10: Patient PAP and RAP changes in response to treatment.
Figure 11:
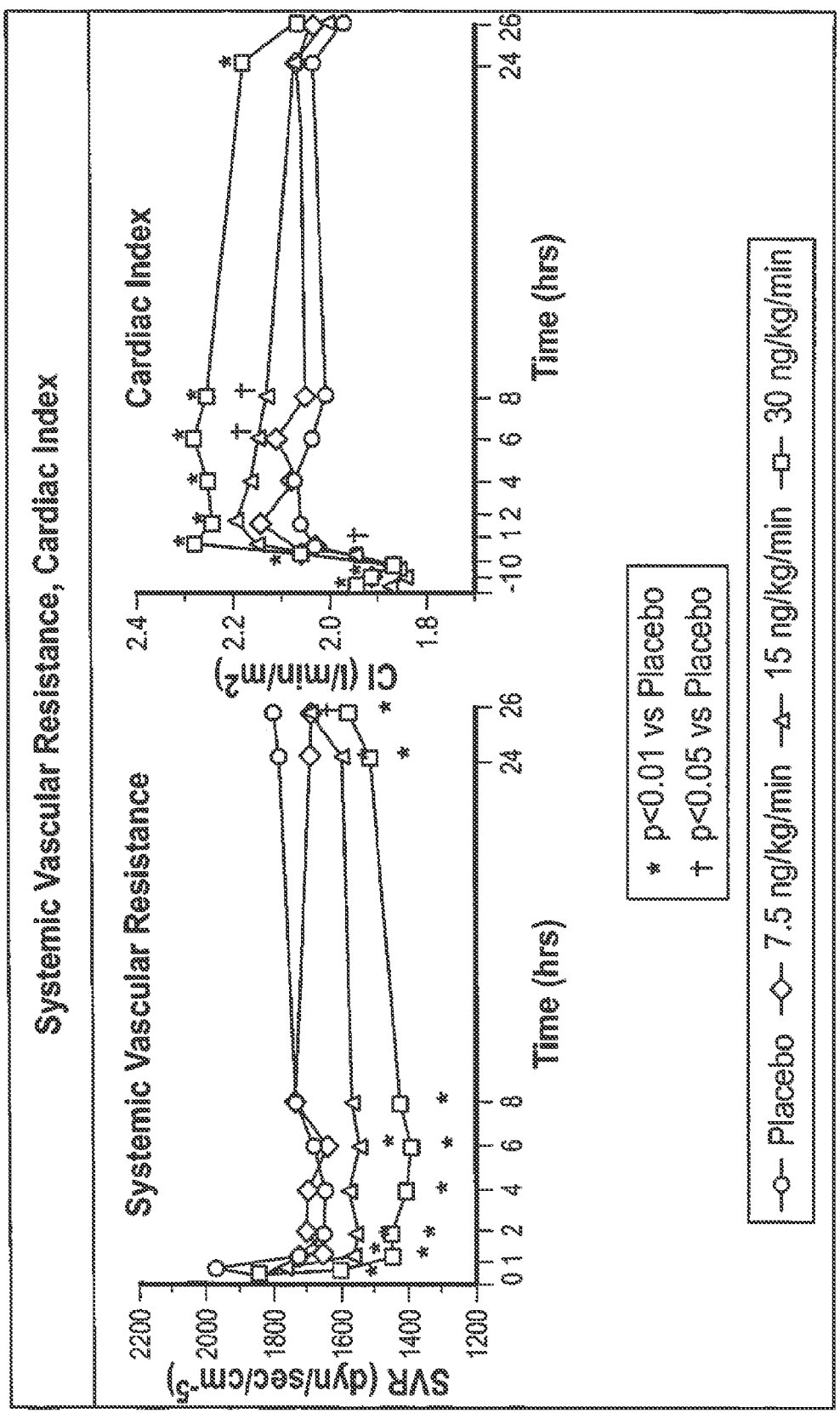
FIG. 11: Patient SVR and CI changes in response to treatment.
Figure 12:
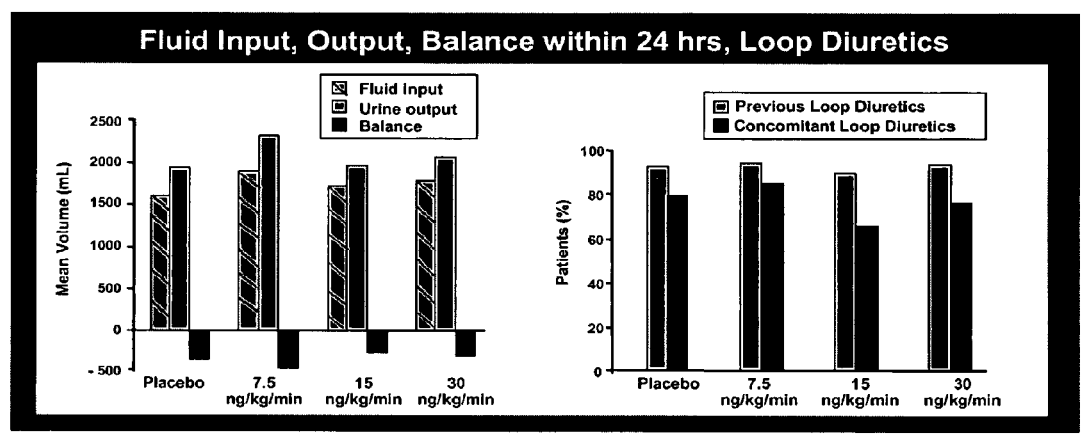
FIG. 12: Patient fluid input, output, balance within 24 hours, loop diuretics.

Left ventricular pump function defined by the relationship of CI and PCWP was improved by ularitide infusion at 6 hours (FIG. 4). Furthermore, myocardial oxygen consumption was decreased in a dose-dependent manner (FIG. 5).

Dyspnea Assessment

After 6 hours of infusion, patients assessed dyspnea relative to baseline. At 6 hours (FIG. 4), all 3 ularitide groups differed significantly from the placebo group. The greatest improvements were seen in the 15 and 30 ng/kg/min groups (P<0.01), while a lesser improvement was observed in the 7.5 ng/kg/min group (P<0.05). More patients in the ularitide groups assessed their changes in dyspnea as moderately or markedly better, whereas no change in dyspnea was reported most frequently in the placebo group. A deterioration in dyspnea was reported only by 1 patient receiving placebo. Furthermore, at 24 hours, more patients receiving ularitide in the 3 different dosages reported an improvement of dyspnea compared to the patients treated with placebo.

Previous and Concomitant Medication

Patients' baseline standard care cardiovascular medication included loop diuretics, thiazide diuretics, nitrates, ACE inhibitors, angiotensin (AT)-II blockers, beta blockers, glycosides, dobutamine, and dopamine. Compared to the preinfusion period, during infusion fewer patients in all 4 treatment groups were treated with diuretics and nitrates, with the most prominent decrease in the 15 ng/kg/min group (Table 5).

NT-proBNP

At baseline, median plasma NT-proBNP levels were pathologically elevated (Table 4). While there was no change at 6 hours in the ularitide groups vs placebo, plasma NT-proBNP significantly decreased in the 15 and 30 ng/kg/min group compared to placebo at 24 hours (P<0.01 and P<0.05, respectively) (FIG. 5).

Renal Effects and Use of Loop Diuretics

Mean urine output did not significantly differ among all treatment groups and ranged from 1,925 to 2,309 mL/24 hours (FIG. 6). However, during dosing, loop diuretics tended to be given less frequently in the 15 ng/kg/min group (67.3%)

compared to the placebo group (79.2%). At baseline, mean serum creatinine (SCr) levels were comparable among all treatment groups. At the end of dosing (24 hours), SCr changes from baseline were relatively unchanged in all treatment groups except the 15 ng/kg/min ularitide group, which tended to display decreased SCr, while creatinine clearance (CLCR) tended to be increased in the placebo group relative to the ularitide groups (FIG. 6). At the end of dosing, the incidence of predefined increases of SCr levels >25% was comparable in all groups. However, in the 15 ng/kg/min group, fewer patients experienced >25% SCr increases at 48 and 72 hours compared to other groups. Through 72 hours, there was also a smaller decrease in CLCR in the 15 ng/kg/min group compared to other groups (FIG. 6).

Safety and Mortality

An overview of safety results is given in Table 7. Adverse events, recorded to 72 hours, were reported more frequently in the ularitide groups, increasing dose-dependently. Compared to placebo (7.5%), the number of patients with any drug-related AEs was higher in the ularitide groups (7.5 ng/kg/min: 16.7%; 15 ng/kg/min: 13.2%; 30 ng/kg/min: 20.0%). Most AEs were of mild to moderate intensity. Most frequently reported drug-related AEs in all ularitide groups were blood pressure decrease (5.4%), hypotension (5.4%), sweating (4.2%), and dizziness (3.0%). All AEs describing any blood pressure decrease as well as hypotension were grouped (blood pressure decrease/hypotension) and incidence rates are given in Table 7. Only 1 patient in each of the ularitide groups required permanent discontinuation of study drug due to decreased blood pressure/hypotension.

Decreased heart rate and bradycardia were reported for 3 patients in the 7.5 ng/kg/min group (5%), for 1 patient (1.8%) in the 30 ng/kg/min group, and for no patients in the 15 ng/kg/min and placebo groups. Increased heart rate/ventricular tachycardia occurred in 2 patients in the 15 ng/kg/min group (3.8%) and tachyarrhythmia was reported in 1 patient in the 30 ng/kg/min group (1.8%). Increased heart rate/ventricular tachycardia or tachyarrhythmia occurred in none of the 7.5 ng/kg/min and placebo patients.

Twelve patients died during the study through day 30: 7 patients (13.2%) in the placebo group, 2 patients (3.4%, P=0.08 compared to placebo) in the 7.5 ng/kg/min group, 2 patients (3.8%, P=0.16) in the 15 ng/kg/min group, and 1 patient (1.8%, P=0.029) in the 30 ng/kg/min group. Most patients died during the follow-up period between days 6 and 26. Nonfatal SAEs were reported for 13 patients: for 2 patients receiving placebo, for 3 patients each in the 7.5 and 15 ng/kg/min groups, and for 5 patients in the 30 ng/kg/min group. For all SAEs, the relationship to the study medication was judged as unlikely or not related. There was a higher number of patients with SAEs in the placebo group compared to the ularitide groups (Table 7).

There were no clinically relevant differences between the treatment groups for laboratory safety parameters. Clinically significant laboratory findings, not already present at pre-dose, were reported for 4 patients: 2 in the 7.5 ng/kg/min group and 2 in the 30 ng/kg/min group, but none in the placebo and 15 ng/kg/min groups. There were no clinically relevant time- or dose-related changes in mean heart rate or ECG intervals. The median time of hospitalization was shorter for the 15 and 30 ng/kg/min groups (122 and 158 hours, respectively) compared with 201 and 192 hours for the placebo and the 7.5 ng/kg/min groups, respectively; this was not statistically significant and requires further evaluation with larger numbers of patients.

Discussion

In the SIRIUS II trial, the synthetic natriuretic peptide ularitide significantly reduced PCWP and improved dyspnea in patients with ADHF when added to standard therapy. Ularitide was well tolerated, with expected dose-dependent decreases in blood pressure. These results suggest that ularitide administered to ADHF patients is clinically and hemodynamically active, without apparent deleterious effects on short-term renal function and 30-day mortality.

Ularitide produced a rapid reduction of PCWP, with results observed within 30 minutes of the start of the infusion in the 15 and 30 ng/kg/min ularitide groups. Concomitantly, ularitide reduced SVR and elevated CI after 1 hour when compared to placebo. Further, at 6 hours, ularitide significantly decreased PCWP in all 3 dose groups compared to standard care, and reduced RAP and SVR, thereby increasing CI. These favorable hemodynamic effects were sustained through the end of the 24-hour infusion period. These data show that ularitide infusion promptly and consistently lowered cardiac filling pressures, leading to a decrease in myocardial oxygen consumption and to improvement of left ventricular pump function.

An additional aim of the trial was to investigate changes in dyspnea, a cardinal symptom in patients with ADHF. Compared to placebo, patients receiving ularitide in all 3 dose groups reported more moderate and marked dyspnea improvements after 6 and 24 hours of infusion. These data support the findings of the pilot SIRIUS I study, in which a similar trend was seen in a smaller number of patients. Although the dyspnea scoring assessment used in SIRIUS II is not validated, it has been commonly used in previous studies. Patient self-assessment may be affected by confounding variables (e.g., if the patient has a right heart catheter in place or if hemodynamic parameters are known). In this trial, we attempted to reduce potential bias by performing dyspnea self-assessment prior to hemodynamic measurements and by prohibiting investigators from discussing these measurements or assisting patients with completing the symptom evaluation. However, knowledge of PCWP by the nursing and medical staff may have still affected a patient's self-assessment.

Reduced cardiac filling pressures lowering ventricular wall stress during ularitide infusions are also reflected in decreased plasma NT-proBNP concentrations. In contrast to placebo, where an increase in plasma NT-proBNP was detected, the 2 higher ularitide doses decreased NT-proBNP at 24 hours. However, the response of NT-proBNP was not seen at 6 hours, but was clearly evident at 24 hours. Abrupt reductions in right and left ventricular filling pressures may result in a reduction of NT-proBNP with a time lag phase shown in a smaller number of patients in the SIRIUS I study. NT-proBNP secretion is controlled at the transcriptional level, usually requiring a longer-term stimulus. Therefore, abrupt reductions in right and left ventricular filling pressures may not directly result in a reduction of NT-proBNP. The half-life of NT-proBNP is 120 minutes, suggesting that hemodynamic changes could be reflected by this test approximately every 12 hours. Since 24 hours was the only measurement made after 6 hours, the possibility of a reduction in NT-proBNP levels earlier than 24 hours cannot be excluded.

Renal function frequently deteriorates during the treatment of patients hospitalized for heart failure, and increases in SCr of only 0.1 mg/dL are independently predictive of worsened outcome. Therefore, agents that improve hemodynamics, leading to beneficial clinical effects but not deteriorating renal function, are needed for ADHF treatment. Ularitide is known to induce renal effects such as diuresis and natriuresis.

Figure 13:
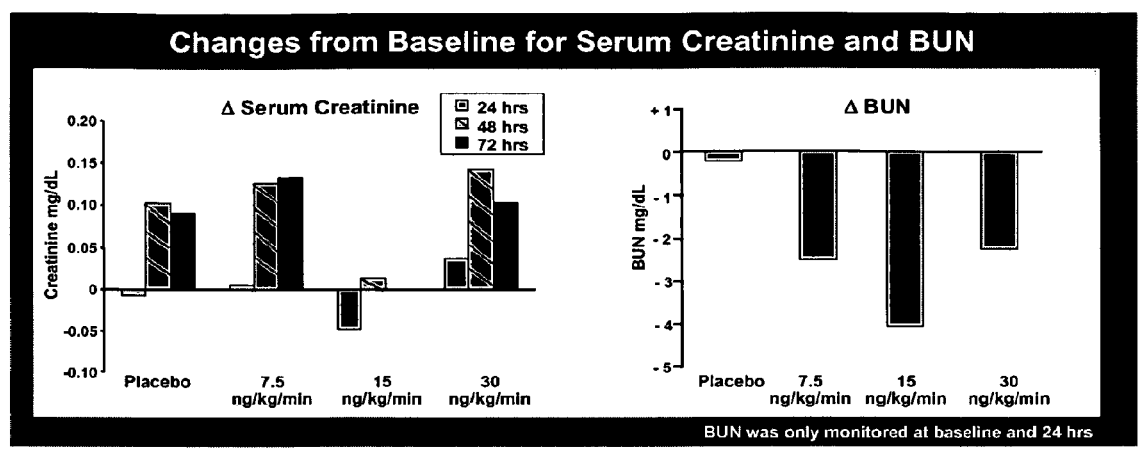
FIG. 13: Patient serum creatinine and BUN changes from baseline in response to treatment.
Figure 14:
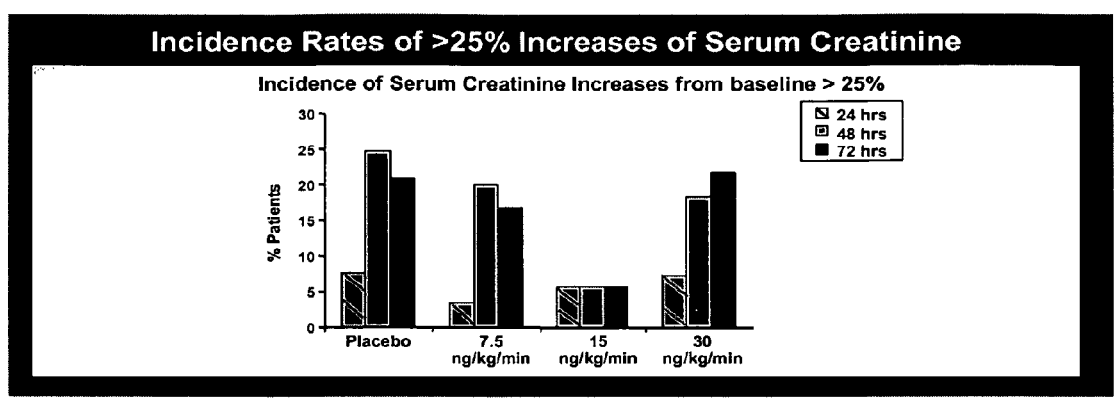
FIG. 14: Patient incidence rates of greater than 25% increase of serum creatinine from baseline.
Figure 15:
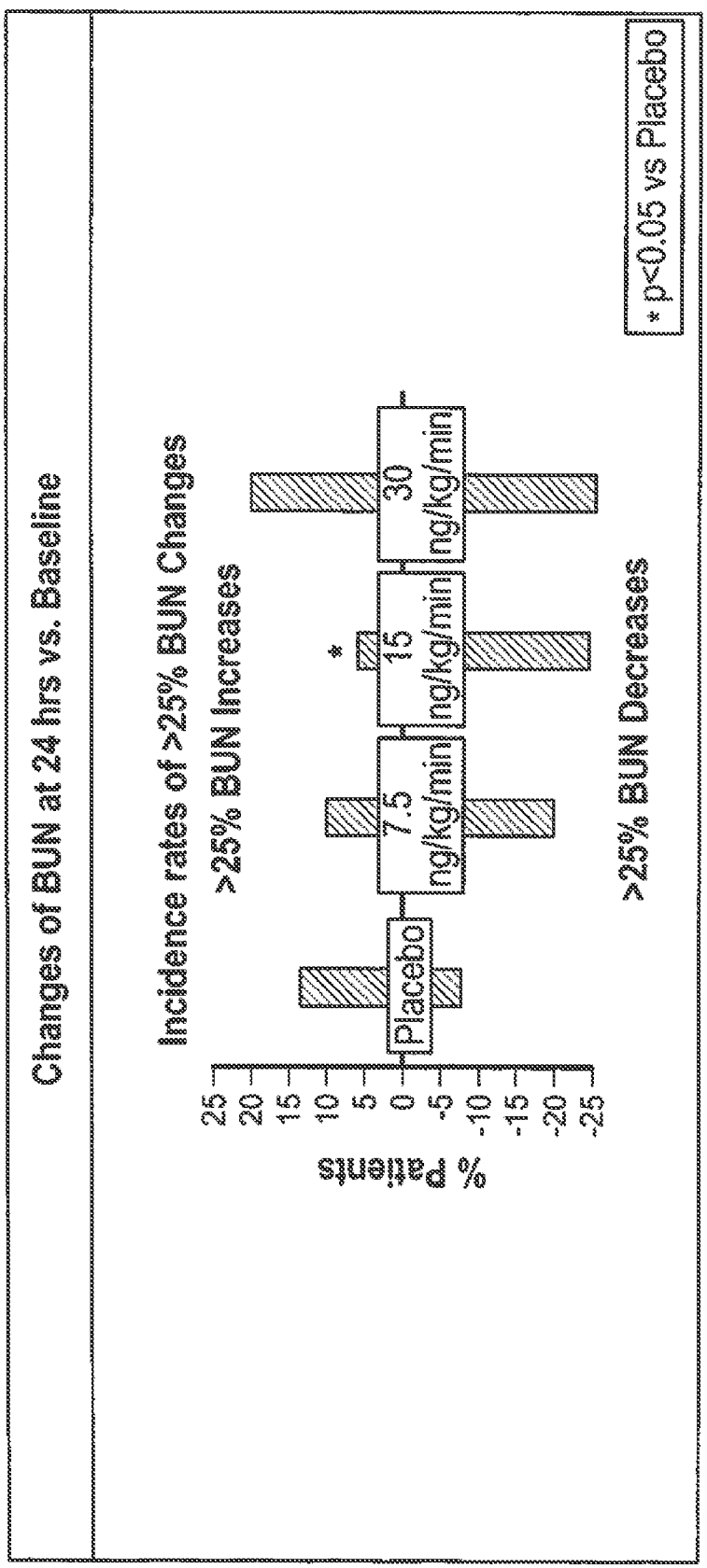
FIG. 15: Patient incidence rates of greater than 25% increase of BUN from baseline.
Figure 16:
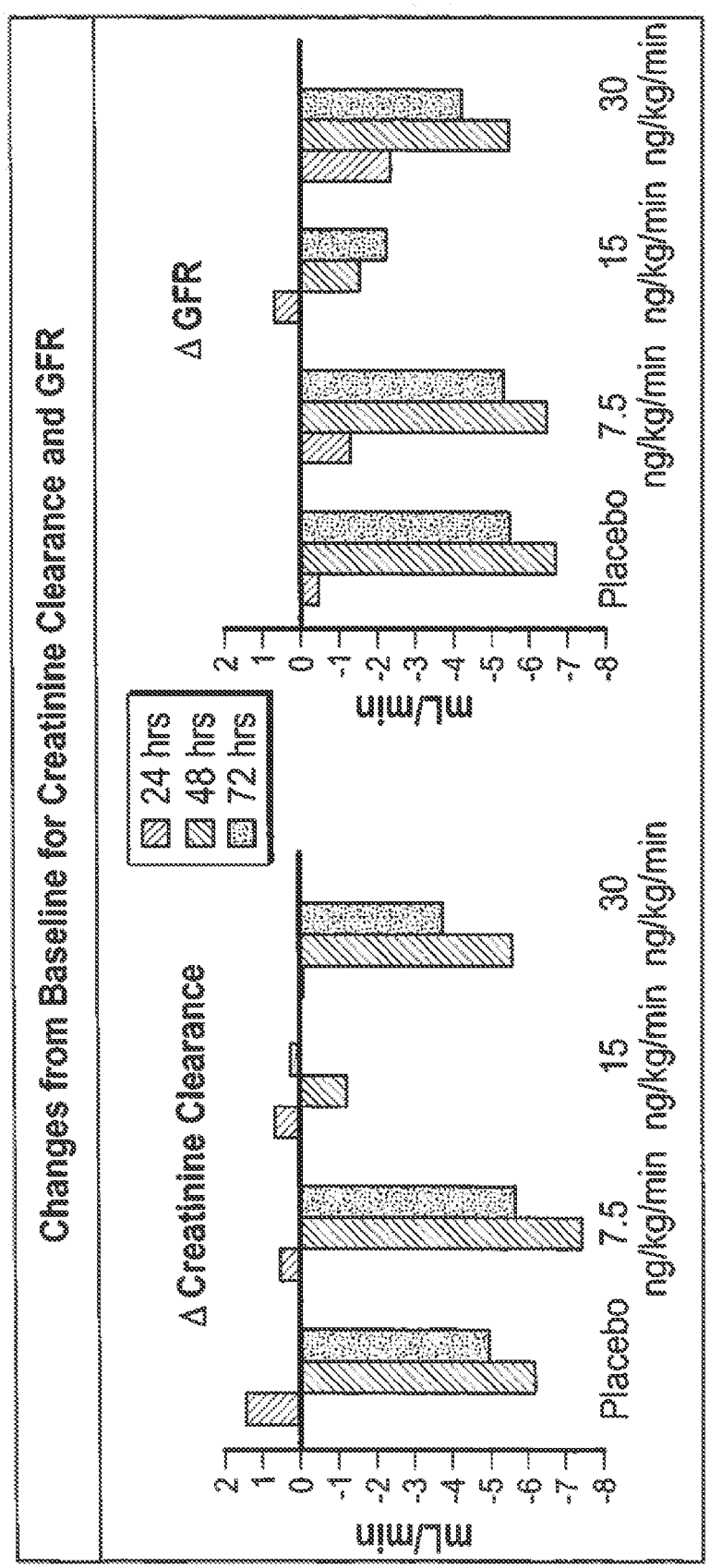
FIG. 16: Patient creatinine clearance and GFR changes from baseline.
Figure 17:
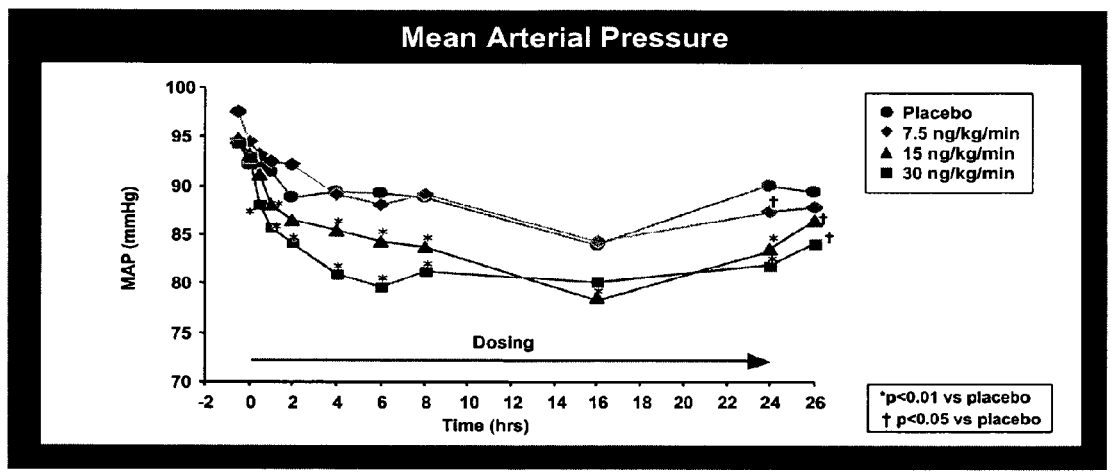
FIG. 17: Patient mean arterial pressure during treatment.

Among the 4 treatment groups, there was no relevant difference in urine output over 24 hours. At 24, 48, and 72 hours, SCr levels were comparable among the placebo, 7.5, and 30 ng/kg/min groups. However, there was a trend toward decreased SCr levels in the 15 ng/kg/min group (FIG. 13). Increases of SCr above 25% occurred less frequently in the 15 ng/kg/min group and CLCR tended to be less decreased in the 15 ng/kg/min group compared to the placebo, 7.5, and 30 ng/kg/min groups (FIG. 14). Taken together, the current data demonstrate no evidence of deleterious renal effects induced by ularitide during the infusion and the 2-day follow-up period. Prospective trials with longer follow-up periods to further investigate the short- and long-term effects of ularitide on renal function are needed. See FIGS. 15 and 16.

Ularitide infusion was well tolerated by patients in all dose groups. The incidence rates of any AE through day 3 were higher in the ularitide groups compared to placebo. SAEs were observed more frequently in the placebo group than in any of the ularitide treatment groups. The most common drug-related AEs were hypotension and blood pressure decrease. Both resolved rapidly either spontaneously or upon IV infusion of physiologic saline. If symptomatic, symptoms were usually mild. As reported previously in other studies, hypotension is the most common AE occurring in heart failure patients when vasodilatory drugs such as ANP, nesiritide, or nitroglycerine are given. In the present study, cardiac arrhythmias including bradycardia or tachycardia occurred at low incidence rates. In an earlier study, ularitide caused bradycardia and severe hypotension in 1 patient with CHF.

The mortality rate was lower in the ularitide groups compared to placebo, and in most patients CHF deterioration was the cause of death. However, these results need to be confirmed in larger trials. The authors are aware of other potential limitations of this study. Bias may be introduced by the use of patient-assessed dyspnea scores, if the PCWP score may possibly be known by either the patient or the observer. In addition, in future studies, adverse events and renal function data should be collected post-hospitalization to investigate longer-term adverse outcomes.

The SIRIUS II trial has demonstrated that a 24-hour infusion of ularitide at all 3 doses in patients with ADHF resulted in prompt, consistent lowering of PCWP and left ventricular pump function improvement associated with improvements in dyspnea. Further, ularitide tended to reduce mortality through day 30 and did not impair renal function during the period of evaluation. We conclude that ularitide is useful for the treatment of patients with ADHF.

Example 4

The effects of continuous intravenous (IV) administration of ularitide over a period of at least 48 hours and up to 72 hours are observed in this study. Participating in this study are adult male and female patients over the age of 18 years, who have been hospitalized for acute decompensated heart failure (ADHF) with dyspnea at rest or with minimal activity.

Following informed consent, patients are randomized to receive either ularitide or placebo (1:1 randomization) administered intravenously for 48 hours to a maximum of 72 hours in this double-blind study. 15 ng/kg/min or 7.5 ng/kg/min ularitide or placebo is given in addition to standard therapy for ADHF. Patients receive the IV administration for at least 48 hours, with the option of extending the treatment beyond 48 hours, to 60 hours or a maximum of 72 hours at the discretion of physicians under pre-specified safety conditions.

Assessments of the patient conditions occur at 1, 3, 6, 24, 48, and 72 hrs, 14 days, 30 days, 60 days, 90 days, 150 days, and 180 days following the start of drug administration. Parameters indicative of hemodynamic, renal, and clinical effects are monitored, which include heart rate, blood pressure, cardiac index (CI), pulmonary capillary wedge pressure (PCWP), ejection fraction (EF), N-terminal pro-brain natriuretic peptide (NT-proBNP), right atrial pressure (RAP), systemic vascular resistance (SVR), serum creatinine, creatinine clearance, blood urea nitrogen (BUN), glomerular filtration rate (GFR), cardiovascular mortality at 30, 60, and 180 days, all-cause mortality at 30, 60, and 180 days, time to death or cardiovascular rehospitalization (other than the index hospitalization for ADHF), days in hospital (index hospitalization), and days alive and not in hospital.

Compared to ularitide administration over a 24-hour time period, a longer administration of at least 48 hours and up to 72 hours maximizes the magnitude of the hemodynamic and clinical effects without increasing adverse effects on patients' kidney function. This longer dosing regimen yields improved short term benefits (e.g., sustained reduction in dyspnea) as well as improved intermediate and long term benefits (e.g., protective effects on the patient's heart and kidney, resulting in reduced incidence of rehospitalization and/or mortality).

All patents, patent applications, and other publications cited in this application, including published amino acid or polynucleotide sequences, are incorporated by reference in the entirety for all purposes.

TABLE 1

Demographics, CHF etiology (mean ± SD), and concomitant cardiac medication during dosing

| | | Urodilatin (ng/[kg · min]) | | |
|---|---|---|---|---|
| | Placebo (n = 6) | 7.5 (n = 6) | 15 (n = 6) | 30 (n = 6) |
| Demographics | | | | |
| Age (y) | 69.8 ± 9.4 | 64.8 ± 12.8 | 66.5 ± 16.8 | 63.5 ± 9.3 |
| Sex (female/male) | 3/3 | 1/5 | 1/5 | 1/5 |
| Weight (kg) | 75.1 ± 8.7 | 88.9 ± 30.8 | 80.2 ± 25.7 | 80.2 ± 16.2 |
| Height (cm) | 169.7 + 9.1 | 169.8 ± 16.5 | 169.2 ± 7.3 | 171.8 ± 12.8 |
| CHF etiology | | | | |
| Dilated cardiomyopathy | 1 | 1 | 1 | 1 |
| Hypertension | 1 | 1 | 2 | — |
| Coronary artery disease | 4 | 4 | 3 | 5 |

TABLE 1-continued

Demographics, CHF etiology (mean ± SD), and concomitant cardiac medication during dosing

| | | Urodilatin (ng/[kg · min]) | | |
|---|---|---|---|---|
| | Placebo (n = 6) | 7.5 (n = 6) | 15 (n = 6) | 30 (n = 6) |
| Cardiac medication | | | | |
| Nitrates | 4 | — | — | 1 |
| Loop diuretics | 6 | 5 | 1 | 2 |
| Dopamine infusion | 1 | 1 | — | — |
| Thiazide diuretics | 1 | 3 | 3 | 3 |
| ACE inhibitors/ATI blockers | 3 | 5 | 5 | 5 |
| B-Blockers | 3 | 5 | 3 | 2 |
| Spironolactone | 3 | 3 | 2 | 2 |
| Glycosides | 3 | 4 | 2 | 2 |

ATI, Angiotensin I.

TABLE 2

Hemodynamic variables (mean changes from baseline after start of study drug infusion (mean ± SD)), serum sodium levels and urinary creatinine levels (mean ± SD)

| | | Urodilatin (ng/[kg · min]) | | |
|---|---|---|---|---|
| | Placebo (n = 6) | 7.5 (n = 6) | 15 (n = 6) | 30 (n = 6) |
| Cardiac index [L/min per m$^2$] | | | | |
| Baseline | 1.9 ± 0.5 | 1.9 ± 0.4 | 1.9 ± 0.3 | 2.0 ± 0.2 |
| 6 h | 0.1 ± 0.3 | −0.0 ± 0.4 | 0.1 ± 0.3 | 0.2 ± 0.2 |
| 24 h | 0.3 ± 0.8 | 0.0 ± 0.2 | 0.2 ± 0.4 | 0.3 ± 0.4 |
| 30 h | −0.0 ± 0.4 | 0.1 ± 0.4 | 0.3 ± 0.4 | −0.0 ± 0.3 |
| Systemic vascular resistance [dyne/s per cm$^{-5}$] | | | | |
| Baseline | 1916 ± 471 | 1718 ± 564 | 1975 ± 551 | 1625 ± 167 |
| 6 h | −201 ± 412 | 104 ± 263 | −50 ± 268 | −276 ± 305 |
| 24 h | −211 ± 557 | 83 ± 363 | −249 ± 376 | −236 ± 348 |
| 30 h | 5 ± 460 | 118 ± 344 | −230 ± 428 | −5 ± 386 |
| Blood pressure systolic (mm Hg) | | | | |
| Baseline | 120.2± | 119.2 ± 18.4 | 130.0 ± 21.0 | 116.3 ± 11.3 |
| 6 h | −7.5 ± 8.6 | −4.0 ± 17.2 | −7.7 ± 5.9 | −16.7 ± 12.0*† |
| 24 h | −8.7 ± 15.2 | −3.5 ± 6.0 | −9.7 ± 10.8 | −10.8 ± 12.3 |
| 30 h | −3.0 ± 10.2 | −1.8 ± 12.0 | −3.0 ± 9.1 | −4.3 ± 19.7 |
| Blood pressure diastolic (mm Hg) | | | | |
| Baseline | 79.0 ± 16.5 | 73.8 ± 12.2 | 79.3 ± 9.7 | 74.3 ± 9.4 |
| 6 h | −4.5 ± 9.6 | 3.0 ± 11.1 | −0.5 ± 6.1 | −10.3 ±11.7 |
| 24 h | −5.3 ± 11.9 | −3.0 ± 11.5 | −6.3 ± 8.7 | −9.8 ± 8.2 |
| 30 h | −2.5 ± 13.8 | 4.2 ± 8.4 | −2.0 ± 7.1 | −6.2 ± 8.4 |
| Heart rate (beat/min) | | | | |
| Baseline | 83.2 ± 16.4 | 79.7 ± 12.0 | 70.2 ± 10.7 | 83.3 ± 5.9 |
| 6 h | −2.5 ± 4.8 | 3.3 ± 14.1 | 5.3 ± 4.5 | −2.5 ± 12.3 |
| 24 h | −9.3 ± 8.9 | 5.0 ± 6.1* | 5.2 ± 4.4* | −0.3 ± 8.2 |
| 30 h | −7.2 ± 12.6 | 3.3 ± 8.6 | 5.5 ± 6.7 | 6.0 ± 8.3 |
| Serum sodium (mmol/L) | | | | |
| Baseline | 138.8 ± 3.2 | 139.7 ± 4.9 | 139.0 ± 1.3 | 137.8 ± 2.8 |
| After 24-h dosing | 138.3 ± 3.9 | 139.4 ± 5.6 | 139.5 ± 2.1 | 134.8 ± 1.7* |
| Urinary creatinine‡ (mgl/L) | | | | |
| Baseline | 90.7 ± 35.3 | 124.6 ± 75.4 | 86.1 ± 53.3 | 46.5 ± 47.9 |
| After 24-h dosing | 62.8 ± 69.3 | 69.5 ± 11.9 | 115.7 ± 48.5 | 117.7 ± 85.7 |

TABLE 2-continued

Hemodynamic variables (mean changes from baseline after start of study drug infusion (mean ± SD)), serum sodium levels and urinary creatinine levels (mean ± SD)

|  | Placebo (n = 6) | Urodilatin (ng/[kg · min]) 7.5 (n = 6) | 15 (n = 6) | 30 (n = 6) |
|---|---|---|---|---|
| Serum creatinine (mg/dL) | | | | |
| Prior dosing | 1.30 ± 0.32 | 1.37 ± 0.97§ | 1.27 ± 0.45 ‖ | 0.93 ± 0.17 |
| End dosing | 1.28 ± 0.34 | 1.66 ± 0.93§ | 1.15 ± 0.32 ‖ | 0.90 ± 0.14 |
| Urine output (mL) | | | | |
| 24 h | 2291 ± 755 | 2156 ± 619 | 1761 ± 969 | 1837 ± 764 |

\*$P < .05$ versus placebo (pairwise contrast).
†$P < .05$ versus 7.5 ng/(kg · min) urodilatin (pairwise contrast).
‡n = 3.
§n = 5.
‖ n = 4.

TABLE 3

Concomitant cardiac medication prior infusion and during infusion

|  |  |  | Prior infusion (24 h) | | During infusion | |
|---|---|---|---|---|---|---|
| Medication | Group | n | No. of patients | Total dose (mg/24 h) | No. of patients | Total dose |
| Loop diuretics | Placebo | 6 | 6 | 550 | 6 | 650 |
|  | 7.5 | 6 | 6 | 480 | 5 | 300 |
|  | 15 | 6 | 3 | 260 | 1 | 60 |
|  | 30 | 6 | 3 | 670 | 2 | 450 |
| Nitrates | Placebo | 6– | 4 | 160 (ISDN) | 4 | 160 (ISDN) |
|  |  |  |  | 24 (MOLS) |  | 24 (MOLS) |
|  |  |  |  | 0.8 (GTN) |  | 0.8 (GTN) |
|  | 7.5 | 6 | — | — | — | — |
|  | 15 | 6 | 1 | 8 (MOLS) | — | — |
|  | 30 | 6 | 1 | 80 (ISDN) | 1 | 80 (ISDN) |
| Thiazide | Placebo | 6 | 1 | 12.5 (HCT) | 1 | 25 (HCT) |
|  | 7.5 | 6 | 3– | 75 (HCT) | 3 | 75 (HCT) |
|  |  |  |  | 40 (XPM) |  | 40 (XPM) |
|  | 15 | 6 | 4 | 50 (HCT) | 3 | 50 (HCT) |
|  |  |  |  | 6 (PTN) |  |  |
|  | 30 | 6 | 3 | 50 (HCT) | 3 | 50 (HCT) |
|  |  |  |  | 20 (XPM) |  | 20 (XPM) |

HCT, hydrochlorothiazide; ISDN, isosorbid dinitrate; GTN, glycerol trinitrate; MOLS, molsidomine; XPM, xiparnid; PTN, piretanid.

TABLE 4

Baseline Demographics, Hemodynamics at Enrollment, and Medical History

|  | Placebo (n = 53) | Ularitide (ng/kg/min) 7.5 (n = 60) | 15 (n = 53) | 30 (n = 55) |
|---|---|---|---|---|
| Demographics mean ± SD | | | | |
| Age (yrs) | 60.6 ± 12.3 | 59.9 ± 13.9 | 59.8 ± 10.8 | 61.5 ± 13.8 |
| Height (cm) | 174.1 ± 8.9 | 174.0 ± 8.7 | 173.7 ± 10.3 | 174.1 ± 9.4 |
| Weight (kg) | 81.0 ± 15.6 | 85.1 ± 16.8 | 83.9 ± 18.0 | 82.7 ± 15.2 |
| Male n (%) | 44 (83.0) | 50 (83.3) | 37 (69.8) | 42 (76.4) |
| Female n (%) | 9 (17.0) | 10 (16.7) | 16 (30.2) | 13 (23.6) |
| Hemodynamics mean ± SD | | | | |
| HR (bpm) | 76.4 ± 12.5 | 77.8 ± 13.9 | 75.5 ± 11.8 | 78.6 ± 14.0 |
| Sys BP (mm Hg) | 127.4 ± 19.9 | 126.1 ± 24.6 | 124.8 ± 17.7 | 124.8 ± 21.6 |
| Dia BP (mm Hg) | 74.5 ± 12.7 | 78.5 ± 13.9 | 77.4 ± 10.7 | 76.7 ± 13.6 |
| CI (L/min/m$^2$) | 1.9 ± 0.4 | 1.9 ± 0.4 | 1.9*0.3 | 1.9 ± 0.4 |

TABLE 4-continued

Baseline Demographics, Hemodynamics at Enrollment, and Medical History

|  | Placebo (n = 53) | Ularitide (ng/kg/min) | | |
|---|---|---|---|---|
|  |  | 7.5 (n = 60) | 15 (n = 53) | 30 (n = 55) |
| PCWP (mm Hg) | 24.9 ± 6.0 | 24.8 ± 5.8 | 25.8 ± 5.8 | 25.4 ± 5.1 |
| EF (≤30%) n (%) | 36 (67.9) | 45 (75) | 42 (79.2) | 37 (67.3) |
| EF (≤40%) n (%) | 50 (94.3) | 57 (95) | 52 (98.1) | 48 (87.3) |
| NT-proBNP (pg/mL), median | 3.06 | 3.52 | 2.64 | 2.94 |
| Cause of Heart Failure n (W) |  |  |  |  |
| ICM | 28 (52.8) | 28 (46.7) | 30 (56.6) | 28 (50.9) |
| DCM | 17 (32.1) | 25 (41.7) | 19 (35.8) | 19 (34.5) |
| HHD | 8 (15.1) | 7 (11.7) | 4 (7.5) | 6 (10.9) |
| Diabetes n (%) | 16 (30.2) | 19 (31.7) | 15 (28.3) | 29 (52.7) |

DCM: dilated cardiomyopathy;
ICM: ischemic cardiomyopathy;
HHD: hypertensive heart disease;
CI: cardiac index;
PCWP: pulmonary capillary wedge pressure;
EF: ejection fraction;
HR: heart rate.

TABLE 5

Previous and Concomitant Cardiac Medication

|  | Previous Medication n (%) | | | | Concomitant Medication During Study Drug Infusion n (%) | | | |
|---|---|---|---|---|---|---|---|---|
|  |  | Ularitide (ng/kg/min) | | |  | Ularitide (ng/kg/min) | | |
| Drug n (%) | Placebo (n = 53) | 7.5 (n = 60) | 15 (n = 52) | 30 (n = 55) | Placebo (n = 53) | 7.5 (n = 60) | 15 (n = 52) | 30 (n = 55) |
| Diuretics | 49 (92.5) | 56 (93.3) | 49 (94.2) | 53 (96.4) | 43 (81.1) | 51 (85.0) | 40 (76.9) | 46 (83.6) |
| Loop Diuretics | 48 (90.6) | 56 (93.3) | 46 (88.5) | 51 (92.7) | 42 (79.2) | 51 (85.0) | 35 (67.3) | 42 (76.4) |
| Nitrates | 25 (47.2) | 26 (43.3) | 31 (59.6) | 21 (38.2) | 16 (30.2) | 20 (33.3) | 19 (36.5) | 15 (27.3) |
| Dobutamine | 2 (3.8) | 1 (1.7) | 4 (7.7) | 1 (1.8) | 1 (1.9) | 0 | 0 | 1 (1.8) |
| Continued at baseline | N.A. | N.A. | N.A. | N.A. | 1 (1.9) |  |  | 1 (1.8) |
| New administration | N.A. | N.A. | N.A. | N.A. |  |  |  |  |
| Dopamine | 1 (1.9) | 4 (6.7) | 4 (7.7) | 3 (5.5) | 1 (1.9) | 1 (1.7) | 1 (1.9) | 3 (5.5) |
| Continued at baseline | N.A. | N.A. | N.A. | N.A. | 1 (1.9) | 1 (1.7) |  | 3 (5.5) |
| New administration | N.A. | N.A. | N.A. | N.A. |  |  | 1 (1.9) |  |
| Digoxin | 22 (41.5) | 38 (63.3) | 35 (67.3) | 37 (67.3) | 17 (32.1) | 32 (53.3) | 29 (55.8) | 34 (61.8) |
| ACE inhibitors | 47 (88.7) | 50 (83.3) | 40 (76.9) | 43 (78.2) | 46 (86.8) | 48 (80.0) | 39 (75.0) | 40 (72.7) |
| AT-11-receptor blockers | 2 (3.8) | 4 (6.7) | 3 (5.8) | 4 (7.3) | 1 (1.9) | 5 (8.3) | 3 (5.8) | 4 (7.3) |
| β Blockers | 39 (73.6) | 49 (81.7) | 35 (67.3) | 37 (67.3) | 35 (66.0) | 47 (78.3) | 36 (69.2) | 33 (60.0) |
| Spironolacton | 27 (50.9) | 41 (68.3) | 36 (69.2) | 36 (65.5) | 28 (52.8) | 40 (66.7) | 37 (71.2) | 35 (63.6) |
| Aspirin | 33 (62.3) | 35 (58.3) | 35 (67.3) | 29 (52.7) | 32 (60.4) | 34 (56.7) | 32 (61.5) | 27 (49.1) |
| Warfarin | 11 (20.8) | 12 (20.0) | 10 (19.2) | 20 (36.4) | 9 (17.0) | 10 (16.7) | 7 (13.5) | 14 (25.5) |

ACE inhibitors: angiotensin-converting enzyme inhibitors; AT-II-receptor blockers: angiotensin II receptor blockers; N.A.: not applicable.

TABLE 6

Hemodynamic Variables: Changes from Baseline

| Hemodynamics mean ± SD | Placebo (n = 53) | Ularitide (ng/kg/min) | | |
|---|---|---|---|---|
|  |  | 7.5 (n = 60) | 15 (n = 52) | 30 (n = 55) |
| Pulmonary Capillary Wedge Pressure (PCWP) [mm Hg] | | | | |
| Baseline | 24.9 ± 6.0 | 24.8 ± 5.8 | 25.8 ± 5.8 | 25.4 ± 5.1 |
| Change at 30 mm | −1.6 ± 3.2 | −1.1 ± 5.3 | −3.2 ± 5.4 | −3.1 ± 5.5 |

TABLE 6-continued

Hemodynamic Variables: Changes from Baseline

| Hemodynamics mean ± SD | Placebo (n = 53) | Ularitide (ng/kg/min) | | |
|---|---|---|---|---|
| | | 7.5 (n = 60) | 15 (n = 52) | 30 (n = 55) |
| 1 h | −2.0 ± 4.7 | −2.9 ± 6.1 | −5.1 ± 5.4** | −5.1 ± 6.4** |
| 4 h | −3.4 ± 5.5 | −6.3 ± 7.6** | −8.9 ± 7.0** | −8.6 ± 5.2** |
| 6 h | −4.4 ± 6.1 | −6.5 ± 7.2* | −10.5 ± 6.3** | −10.1 ± 5.7** |
| 24 h | −5.2 ± 7.3 | −7.9 ± 9.2* | −9.9 ± 7.6** | −8.8 ± 7.0** |
| 26 h | −4.4 ± 6.2 | −6.4 ± 9.1 | −7.0 ± 8.1 | −7.4 ± 6.7* |
| Cardiac Index (CI) [L/min per m$^2$] | | | | |
| Baseline | 1.9 ± 0.4 | 1.9 ± 0.4 | 1.9 ± 0.4 | 1.9 ± 0.4 |
| Change at 30 min | 0.01 ± 0.2 | 0.07 ± 0.3 | 0.1 ± 0.2 | 0.2 ± 0.3 |
| 1 h | 0.1 ± 0.3 | 0.1 ± 0.2* | 0.3 ± 0.3** | 0.4 ± 0.3** |
| 4 Ii | 0.2 ± 0.3 | 0.1 ± 0.4 | 0.3 ± 0.4 | 0.4*0.4** |
| 6 h | 0.1 ± 0.3 | 0.2 ± 0.4 | 0.3 ± 0.4* | 0.4 ± 0.5** |
| 24 h | 0.1 ± 0.3 | 0.1 ± 0.4 | 0.2 ± 0.4 | 0.3 ± 0.4* |
| 26 h | 0.04 ± 0.3 | 0.1 ± 0.4 | 0.2 ± 0.4 | 0.2 ± 0.4* |
| Systemic Vascular Resistance (SVR) [dyn/sec per cm$^{-5}$] | | | | |
| Baseline | 1823 ± 464 | 1872 ± 662 | 1915 ± 556 | 1840 ± 644 |
| Change at 30 mm | −24 ± 254 | −96 ± 496 | −142 ± 329 | −230 ± 432 |
| 1 h | −90 ± 324 | −136 ± 315 | −364 ± 415** | −392 ± 374** |
| 4 h | −173 ± 335 | −131*435 | −334 ± 288 | −423 ± 464** |
| 6 h | −140 ± 315 | −184 ± 373 | −375 ± 444** | −445 ± 428** |
| 24 h | −30 ± 473 | .135 ± 541 | −328 ± 420** | −321 ± 542** |
| 26 h | −16 ± 386 | −131 ± 490 | −232 ± 448* | −268 ± 478** |
| Right Atrial Pressure (RAP) [mm Hg] | | | | |
| Baseline | 9.6 ± 5.2 | 11.3 ± 6.6 | 10.0 ± 5.1 | 12.0 ± 7.4 |
| Change at 30 mm | −0.2 ± 3.3 | −1.2 ±*4.6 | −0.7 ± 2.6 | −1.9 ± 4.9 |
| 1 h | −0.8 ± 3.4 | −1.8 ± 4.9 | −1.1 ± 3.6 | −2.4 ± 4.6 |
| 4 h | −0.9 ± 4.3 | −3.0 ± 5.7* | −3.3 ± 3.3** | −4.4 ± 4.4** |
| 6 h | −0.6 ± 4.5 | −3.5 ± 5.6** | −3.9 ± 3.6** | −5.0 ± 5.3** |
| 24 h | −1.6 ± 4.9 | −4.1 ± 5.5* | −3.3 ± 4.2 | −4.7 ± 6.2* |
| 26 h | −1.8 ± 5.2 | −3.0 ± 6.6 | −2.3 ± 4.7 | −3.4 ± 6.0 |
| Systolic Blood Pressure [mm Hg] | | | | |
| Baseline | 127.4 ± 19.9 | 126.1 ± 24.6 | 124.8 ± 17.7 | 124.8 ± 21.6 |
| Change at 30 mm | −3.9 ± 7.3 | −1.8 ± 11 | −2.5 ± 11.6 | −1.4 ± 10.6 |
| 1 h | −3.2 ± 8.5 | −2.7 ± 11.3 | −5.4 ± 12.4 | −5.8 ± 13.5 |
| 4 h | −5.8 ± 13.0 | −6.9 ± 11.9 | −9.0 ± 12.5 | −13.4 ± 14.0** |
| 6 h | −5.4 ± 12.8 | −7.4 ± 11.1 | −11.3 ± 12.8** | −14.6*12.3** |
| 24 h | −4.8 ± 15.8 | −8.8 ± 16.4 | −12.1 ± 14.8** | −12.2 ± 18.0** |
| 26 h | −6.1 ± 14.6 | −7.9 ± 16.7 | −9.4 ± 14.8 | −8.8 ± 17.9 |

*$P < .05$,
**$P < .01$, ANOVA of the changes from baseline versus placebo.

TABLE 7

Adverse Events

| | Placebo (n = 53) | Ularitide (ng/kg/min) | | |
|---|---|---|---|---|
| | | 7.5 (n = 60) | 15 (n = 53) | 30 (n = 55) |
| Subjects with any AE Day 1-3 n (%) | 11 (20.8) | 17 (28.3) | 13 (24.5) | 24 (43.6) |
| Subjects with any drug-related AE Day 1-3 n (%) | 4 (7.5) | 10 (16.7) | 7 (13.2) | 11 (20.0) |
| Subjects with BP Decrease/hypotension Day 1-3 n (%) | 2 (3.8) | 5 (8.3) | 7 (13.2) | 9 (16.4) |
| Subjects with BP decrease/hypotension during infusion n (%) | 1 (1.9) | 5 (8.3) | 6 (11.3) | 9 (16.4) |
| Symptomatic | 1 (1.9) | 4 (6.7) | 3 (5.7) | 4 (7.3) |
| Asymptomatic | 0 (0) | 1 (1.7) | 3 (5.7) | 5 (9.1) |
| Subjects with infusions discontinued due to hypotension n (%) | 0 (0) | 3 (5.0) | 4 (7.5) | 8 (14.5) |
| Subjects with any SAE Day 1-30 n (%) | 9 (17.0) | 5 (8.3) | 5 (9.4) | 6 (10.9) |
| Deaths Day 1-30 n (%) | 7 (13.2) | 2 (3.3) | 2 (3.8) | 1 (1.8) |
| Day 1-3 | 2 (3.8) | 0 (0) | 0 (0) | 1 (1.8) |
| Day 3-30 | 5 (9.4) | 2 (3.3) | 2 (3.8) | 0 (0) |

What is claimed is:

1. A method for treating acute decompensated heart failure (ADHF) or decompensated heart failure (DHF), comprising administering to a patient in need thereof a composition comprising an effective amount of urodilatin continuously for a time period ranging from 24 hours to 72 hours, wherein urodilatin is administered at a rate ranging from 7.5 ng/(kg·min) to about 100 ng/(kg·min).

2. The method of claim 1, wherein the composition is administered intravenously.

3. The method of claim 1, wherein the time period is between 24 to 48 hours.

4. The method of claim 1, wherein the time period is between 48 to 72 hours.

5. The method of claim 2, wherein urodilatin is administered at the rate of 7.5 ng/(kg·min).

6. The method of claim 1, wherein urodilatin is administered at the rate of 15 ng/(kg·min).

7. The method of claim 1, wherein urodilatin is administered at the rate of 30 ng/(kg·min).

8. The method of claim 1, wherein urodilatin is administered at the rate of 45 ng/(kg·min).

9. The method of claim 1, wherein urodilatin is administered at the rate of 60 ng/(kg·min).

10. The method of claim 1, wherein urodilatin is administered at the rate of 100 ng/(kg·min).

11. The method of claim 2, wherein the composition further comprises mannitol.

12. The method of claim 1, wherein the composition further comprises an aqueous diluent.

13. The method of claim 12, wherein the aqueous diluent comprises a NaCl aqueous solution.

14. The method of claim 1, wherein the composition further comprises a surfactant.

15. The method of claim 1, wherein the composition further comprises a preservative.

16. The method of claim 1, wherein the composition further comprises antibacterial and antifungal agents.

17. The method of claim 1, wherein the composition further comprises an agent delaying absorption.

18. The method of claim 1, wherein administration does not include an initial bolus.

19. A method for treating acute decompensated heart failure (ADHF) or decompensated heart failure (DHF), comprising administering to a patient in need thereof a composition comprising: an effective amount of urodilatin and mannitol, continuously for a time period ranging from 24 hours to 72 hours, wherein urodilatin is administered at a rate ranging from 7.5 ng/(kg·min) to about 100 ng/(kg·min).

* * * * *